(12) United States Patent
Hartz et al.

(10) Patent No.: US 8,372,847 B2
(45) Date of Patent: Feb. 12, 2013

(54) PYRAZINONE MODULATOR OF CORTICOTROPIN-RELEASING FACTOR RECEPTOR ACTIVITY

(75) Inventors: Richard A. Hartz, Middletown, CT (US); Vijay T. Ahuja, Middletown, CT (US); Vivekananda M. Vrudhula, Killingworth, CT (US); Joanne J. Bronson, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/052,458

(22) Filed: Mar. 21, 2011

(65) Prior Publication Data

US 2011/0166160 A1    Jul. 7, 2011

Related U.S. Application Data

(63) Continuation of application No. 12/429,810, filed on Apr. 24, 2009, now Pat. No. 7,932,256.

(60) Provisional application No. 61/085,230, filed on Jul. 31, 2008.

(51) Int. Cl.
    *A61K 31/4965*    (2006.01)
(52) U.S. Cl. ................................. 514/255.06
(58) Field of Classification Search .............. 514/255.06
    See application file for complete search history.

(56) References Cited

U.S. PATENT DOCUMENTS 6,159,980 A    12/2000    Arvanitis et al.

FOREIGN PATENT DOCUMENTS

WO    WO 2004/046136    6/2004

OTHER PUBLICATIONS

Mitchell, Neurosci. Biobehav. Rev. 22(5); 635-651, 1998.*
Kehne, J. H., CNS Neurol Disord Drug Targets, 693): 163-182, 2007.*
Hackam, D.G. et al., "Translation of Research Evidence from Animals to Humans", JAMA, vol. 296, No. 14, pp. 1731-1732 (2006).
Jordan, V.C., "Tamoxifen: A Most Unlikely Pioneering Medicine", Nature Reviews, vol. 2, pp. 205-213 (2003).

* cited by examiner

*Primary Examiner* — Shirley V Gembeh
(74) *Attorney, Agent, or Firm* — James Epperson

(57) ABSTRACT

The invention relates to the compound (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile, pharmaceutical compositions of the compound, and methods of using the compound for the treatment of psychiatric disorders and neurological diseases including depression, anxiety related disorders, irritable bowel syndrome, addiction and negative aspects of drug and alcohol withdrawal, and other conditions associated with CRF.

5 Claims, No Drawings

PYRAZINONE MODULATOR OF CORTICOTROPIN-RELEASING FACTOR RECEPTOR ACTIVITY

CROSS-REFERENCE TO RELATED APPLICATIONS

This application is a Continuation of U.S. Non-Provisional application Ser. No. 12/429,810 filed Apr. 24, 2009 which claims the benefit of U.S. Provisional Application Ser. No. 61/085,230 filed Jul. 31, 2008.

BACKGROUND OF THE INVENTION

The invention relates to the compound (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile, pharmaceutical compositions of the compound, and methods of using the compound for the treatment of psychiatric disorders and neurological diseases including depression, anxiety related disorders, irritable bowel syndrome, addiction and negative aspects of drug and alcohol withdrawal, and other conditions associated with CRF.

Corticotropin releasing factor (CRF), a 41 amino acid peptide, is the primacy physiological regulator of proopiomelanocortin (POMC) derived peptide secretion from the anterior pituitary gland [Rivier, J. et al., *Proc. Nat. Acad. Sci. (USA)* 80: 4851 (1983); Vale, W. et al., *Science* 213: 1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [Vale, W. et al., *Rec. Prog. Horm. Res.* 39: 245 (1983); Koob, G. F. *Persp. Behav. Med.* 2: 39 (1985); De Souza, E. B. et al., *J. Neurosci.* 5: 3189 (1985)]. There is evidence that CRF plays a significant role in integrating the response of the immune system to physiological, psychological, and immunological stressors [Blalock, J. E. *Physiological Reviews* 69: 1 (1989); Morley, J. E. *Life Sci.* 41: 527 (1987)].

Over-expression or under-expression of CRF has been proposed as an underlying cause for several medical disorders. Such treatable disorders include affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorders, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia, hypertension, tachycardia and congestive heart failure, stroke, osteoporosis, premature birth, psychosocial dwarfism, stress-induced fever, ulcer, diarrhea, post-operative ileus and colonic hypersensitivity associated with psychopathological disturbance and stress [for reviews see McCarthy, J. R.; Heinrichs, S. C.; Grigoriadis, D. E. *Cur. Pharm. Res.* 5: 289-315 (1999); Gilligan, P. J.; Robertson, D. W.; Zaczek, R. *J. Med. Chem.* 43: 1641-1660 (2000), Chrousos, G. P. *Int. J. Obesity,* 24, Suppl. 2, S50-S55 (2000); Webster, E.; Torpy, D. J.; Elenkov, I. J.; Chrousos, G. P. *Ann. N.Y. Acad. Sci.* 840: 21-32 (1998); Newport, D. J.; Nemeroff, C. B. *Curr. Opin. Neurobiology,* 10: 211-218 (2000); Mastorakos, G.; Ilias, I. *Ann. N.Y. Acad. Sci.* 900: 95-106 (2000); Owens, M. J.; Nemeroff, C. B. *Expert Opin. Invest. Drugs* 8: 1849-1858 (1999); Koob, G. F. *Ann. N.Y. Acad. Sci.,* 909: 170-185 (2000)].

There is evidence that CRF plays a role in affective disorders including depression (for example, major depression, single episode depression, recurrent depression, child abuse induced depression, and postpartum depression), dysthemia, bipolar disorders, and cyclothymia. In individuals afflicted with major depression, the concentration of CRF is significantly increased in the cerebrospinal fluid (CSF) of drug-free individuals [Nemeroff, C. B. et al., *Science* 226: 1342 (1984); Banki, C. M. et al., *Am. J. Psychiatry* 144: 873 (1987); France, R. D. et al., *Biol. Psychiatry* 28: 86 (1988); Arato, M. et al., *Biol Psychiatry* 25: 355 (1989)]. Furthermore, the density of CRF receptors is significantly decreased in the frontal cortex of suicide victims, consistent with a hypersecretion of CRF [Nemeroff, C. B. et al., *Arch. Gen. Psychiatry* 45: 577 (1988)]. In addition, there is a blunted adrenocorticotropin (ACTH) response to CRF (i.v. administered) observed in depressed patients [Gold, P. W. et al., *Am J. Psychiatry* 141: 619 (1984); Holsboer, F. et al., *Psychoneuroendocrinology* 9: 147 (1984); Gold, P. W. et al., *New Eng. J. Med.* 314: 1129 (1986)]. Preclinical studies in rats and non-human primates provide additional support for the hypothesis that hypersecretion of CRF may be involved in the symptoms seen in human depression [Sapolsky, R. M. *Arch. Gen. Psychiatry* 46: 1047 (1989)]. There is preliminary evidence that tricyclic antidepressants can alter CRF levels and thus modulate the numbers of CRF receptors in brain [Grigoriadis et al., *Neuropsychopharmacology* 2: 53 (1989)].

There is evidence that CRF plays a role in the etiology of anxiety and related disorders including anxiety with co-morbid depressive illness, panic disorder, phobic disorders, social anxiety disorder, obsessive-compulsive disorder, post-traumatic stress disorder, and atypical anxiety disorders [The Merck Manual of Diagnosis and Therapy, 16$^{th}$ edition (1992)]. Emotional stress is often a precipitating factor in anxiety disorders, and such disorders generally respond to medications that lower response to stress. Excessive levels of CRF are known to produce anxiogenic effects in animal models [see Britton, D. R. et al., *Life Sci.* 31: 363 (1982); Berridge, C. W., Dunn, A. *J. Regul. Peptides* 16: 83 (1986); Berridge, C. W.; Dunn, A. *J. Horm. Behav.* 21: 393 (1987)]. CRF produces anxiogenic effects in animals and interactions between benzodiazepine/non-benzodiazepine anxiolytics and CRF have been demonstrated in a variety of behavioral anxiety models [Britton, D. R. et al., *Life Sci.* 31: 363 (1982); Berridge, C. W., Dunn, A. *J. Regul. Peptides* 16: 83 (1986)]. Preliminary studies using the putative CRF receptor antagonist α-helical ovine CRF (9-41) in a variety of behavioral paradigms demonstrate that the antagonist produces "anxiolytic-like" effects that are qualitatively similar to the benzodiazepines [Berridge, C, W.; Dunn, A. *J. Horm. Behav.* 21: 393 (1987), Dunn, A. J.; Berridge, C. W. *Brain Research Reviews* 15: 71 (1990)].

Neurochemical, endocrine, and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [Britton, K. T. et al. *Psychopharmacology* 86: 170 (1985); Britton, K. T. et al. *Psychopharmacology* 94: 306 (1988)] and in the acoustic startle test [Swerdlow, N. R. et al. *Psychopharmacology* 88: 147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [Britton, K. T. et al. *Psychopharmacology* 94: 306 (1988)]. Of particular interest is that preliminary studies examining the effects of a CRF receptor antagonist (α-helical CRF9-41) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p 221 (1990)].

In addition to modulating the HPA-axis, CRF is considered to be a key modulator of the gut-brain axis. Evidence exists indicating that CRF may play a role in mediating stress-related gastrointestinal disorders [Gabry, K. E. et al. *Molecular Psychiatry* 7(5): 474-483 (2002)] such as irritable bowel syndrome (IBS), post-operative ileus, and colonic hypersensitivity associated with psychopathological disturbance and stress [for reviews see E. D. DeSouza, C. B. Nemeroff, Editors; *Corticotropin-Releasing Factor: Basic and Clinical Studies of a Neuropeptide*, E. B. De Souza and C. B. Nemeroff eds., CRC Press p 221 (1990) and Maillot, C. et al. *Gastroenterology*, 119: 1569-1579 (2000); Fukudo, S. *J. Gastroenterol.* 42(Suppl XVII): 48 (2007); Taché, Y.; Bonaz, B. *J. Clin. Invest.* 117: 33 (2007)]. In rats it has been demonstrated that i.p. administration of $CRF_1$ antagonist JTC-017 blocked an increase in fecal output induced by exposure to chronic colorectal distention [Saito, K. et al. *Gastroenterol.*, 129: 1533 (2005)]. Additionally, JTC-017 attenuated the anxiety-related behavior seen after exposure to acute colorectal distention. CRF-stimulated colonic motility in rats was also attenuated by central administration of $CRF_{1/2}$ peptide antagonist astressin [Tsukamoto, K. et al. *Am. J. Physiol. Regul. Integr. Camp. Physiol.* 290: 81537 (2006)]. In healthy humans, i.v. administration of CRF was shown to affect rectal hypersensitivity and mimic a stress-induced visceral response specific to IBS patients [Nozu, T.; Kudaira, M. *J. Gastroenterol.* 41: 740 (2006)]. These data suggest that CRF antagonists may be useful for the treatment of IBS.

Antagonists of $CRF_1$ have been examined for use as treatments for addiction and the negative aspects of drug withdrawal [Steckler, T.; Dautzenberg, F. M. *CNS Neural. Disord. Drug Targets* 5: 147 (2006)]. Withdrawal from nicotine, cocaine, opiates, and alcohol often leads to a negative emotional state and elevated levels of anxiety. These undesirable effects can sometimes be counteracted by increasing self-administration of the substance, which leads to relapse to the addicted state. External stressors can often lead to a relapse in abuse as well.

CRF receptor antagonists may be useful for treatment of the negative affective aspects of withdrawal from nicotine. Pretreatment of nicotine dependent rats with $CRF_{1/2}$ peptide antagonist D-Phe $CRF_{(12-41)}$ was shown to prevent the elevations in brain reward threshold associated with nicotine withdrawal [Bruijnzeel, A. W. et al. *Neuropsychopharmacol.* 32: 955 (2007)]. D-Phe $CRF_{(12-41)}$ also caused a decrease in stress-induced reinstatement of nicotine-seeking behavior in rats [Zislis, G. et al. *Neuropharmacol.* 53: 958 (2007)]. Additionally, an increase in nicotine intake after a period of abstinence, often seen with nicotine dependence, could be blocked in rats by pretreatment with the $CRF_1$ antagonist MPZP [Specio, S. E. et al. *Psychopharmacol.* 196: 473 (2008); George, O. et al. *Proc. Natl. Acad. Sci. U.S.A.* 104: 17198 (2007)].

Evidence from animal studies also suggests that the effects of cocaine and morphine withdrawal and relapse may be attenuated by antagonism of the CRF receptor. The $CRF_1$ antagonist CP-154,526 was shown to attenuate spiradoline-induced reinstatement of cocaine seeking behavior in squirrel monkeys [Valdez, G. R. et al. *J. Pharm. Exp. Ther.* 323: 525 (2007)] as well as cue-induced reinstatement of methamphetamine-seeking behavior in rats [Moffett, M. C. et al. *Psychopharmacol.* 190: 171 (2007)]. Lorazepam dependent rats pretreated with $CRF_1$ antagonist R121919 [Holsboer, F. et al. *Eur. J. Pharmacol.* 583: 350 (2008)] before precipitation of withdrawal showed reduced HPA axis activation and reduced anxiety behaviors in the defensive withdrawal model [Skelton, K. H. et al. *Psychopharmacol.* 192: 385 (2007)]. R121919 was similarly able to attenuate the severity of precipitated morphine withdrawal and withdrawal-induced HPA axis activation [Skelton, K. H. et al. *Eur. J. Pharmacol.* 571: 17 (2007)]. The amount of opiate exposure during self-administration as well as the length of abstinence can affect relapse. Rats allowed to self-administer cocaine for longer periods of time (6 h daily) were more susceptible to reinstatement by cocaine, electric foot shock, or administered CRF than those allowed to self-administer for shorter periods (2 h daily) [Mantsch, J. R. et al. *Psychopharmacol.* 195: 591 (2008)]. In another study, $CRF_1$ antagonists MPZP and antalarmin were shown to reduce cocaine self-administration in rats with extended daily cocaine access [Specio, S. E. *Psychopharmacol.* 196: 473 (2008)].

There is evidence suggesting that $CRF_1$ antagonists may help block the negative emotional aspects, excessive alcohol drinking, and stress-induced relapse seen in ethanol dependence [Heilig, M. et al. *Trends Neurosci.* 30: 399 (2007)]. Ethanol-dependent wild-type mice show an increase in ethanol self-administration during withdrawal, but only after a period of abstinence [Chu, K. G. F. *Pharmacol. Biochem. Behav.* 86: 813 (2007)]. This effect was reversed by administration of the $CRF_1$ antagonist antalarmin. $CRF_1$ knockout (KO) mice do not show this tendency toward increased self-administration. When treated with $CRF_1$ antagonists R121919 or antalarmin, ethanol-dependent rats showed a reduction in excessive ethanol self-administration during acute withdrawal [Funk, C. K. et al. *Biol. Psychiatry* 61: 78 (2007)]. Non-dependent rats treated with these $CRF_1$ antagonists, however, showed no effect on ethanol self-administration. Similarly, $CRF_1$ antagonist MPZP selectively reduced excessive ethanol self-administration during acute withdrawal in dependent rats [Richardson, H. N. et al. *Pharmacol. Biochem. Behav.* 88: 497 (2008)]. In another study, a novel $CRF_1$ antagonist selectively reduced excessive ethanol self-administration induced by stress in dependent rats [Gehlert, D. R. et al. *J. Neurosci.* 27: 2718 (2007)]. These studies demonstrate that antagonism of $CRF_1$ receptors can selectively block excessive ethanol self-administration without affecting basal self-administration levels. This suggests that $CRF_1$ antagonists could be useful for the treatment of alcohol dependence.

It has been further postulated that CRF has a role in cardiovascular or heart-related diseases arising from stress such as hypertension, tachycardia and congestive heart failure, stroke (methods for using $CRF_1$ antagonists to treat congestive heart failure are described in U.S. patent application Ser. No. 09/248,073, filed Feb. 10, 1999, now U.S. Pat. No. 6,043, 260 (Mar. 28, 2000).

It has also been suggested that $CRF_1$ antagonists are useful for treating arthritis and inflammation disorders [Webster, E. L. et al. *J. Rheumatol.* 29(6): 1252-61 (2002); Murphy, E. P. et al. *Arthritis Rheum.* 44(4): 782-93 (2001)].

It has also been suggested that $CRF_1$ antagonists are useful for skin disorders [Zouboulis, C. C. et al. *Proc. Natl. Acad. Sci.* 99: 7148-7153 (2002)]. Stress-induced exacerbation of chronic contact dermatitis was blocked by a selective $CRF_1$ antagonist in an animal model, suggesting that $CRF_1$ is involved in the stress-induced exacerbation of chronic contact dermatitis and that $CRF_1$ antagonist may be useful for treating this disorder [Kaneko, K. et al. *Exp. Dermatol*, 12(1): 47-52 (2003)].

Studies have demonstrated that $CRF_1$ antagonists may be useful as hair growth stimulators (WO2002/19975 discloses cell culture assays for the use of CRF antagonists in stimulating KBM-2 cell production). Thus, CRF antagonists may be useful in treatment of hair loss.

DESCRIPTION OF THE INVENTION

The invention encompasses (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile (Compound I) and pharmaceutical compositions and methods for modulating CRF in patients with medical conditions associated with aberrant levels of CRF.

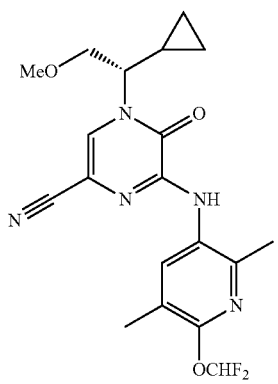

I

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

As Compound I possesses an asymmetric carbon atom, the invention includes the racemate as well as the individual enantiometric forms of Compound I and chiral and racemic intermediates as described herein. The use of a single designation such as (R) or (S) is intended to include mostly one stereoisomer. Mixtures of isomers can be separated into individual isomers according to methods known in the art.

"Treatment," "therapy," "regimen," and related tee is are used as understood by medical practitioners in the art.

"Therapeutically effective" means the amount of agent required to provide a meaningful patient benefit as understood by medical practitioners in the art. When applied to an individual active ingredient, administered alone, the term refers to that ingredient alone. When applied to a combination, the term refers to combined amounts of the active ingredients that result in the therapeutic effect, whether administered in combination, serially or simultaneously.

"Patient" means a person suitable for therapy as understood by medical practitioners in the art.

Synthetic Methods

Compound I can be prepared by methods known in the art including those described in Schemes 1-8, Reasonable variations of the described procedures, together with synthetic methods which would be evident to one skilled in the art, are intended to be within the scope of the present invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "$Et_2O$" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Two routes for the synthesis of the (S)-amine (9) are shown in Schemes 1 and 2. In Route A (Scheme 1), the (S)-chiral center in the amine can be established by a Strecker synthesis involving diastereoselective addition of cyanide to the chiral imine 4 (Bayston, D. J.; Griffin, J. L. W.; Gruman, A.; Polywka, M. E. C.; Scott, R. M. U.S. Pat. No. 6,191,306). Imine 4 in turn can be derived from the commercially available chiral amine 3. In Route B, the chiral amine can be obtained from racemic intermediate 13 by chiral chromatographic separation.

Route A starts with condensation of commercially available cyclopropane carboxaldehyde 2 and (S)-1-phenethyl amine 3 and can provide the chiral imine 4. Treatment in situ with potassium cyanide, followed by hydrolysis of the intermediate α-amino nitrile 5 under acidic conditions can generate acid 6. Borane reduction of 6 can afford alcohol 7, which can be methylated by treatment with sodium hydride and methyl iodide to provide the ether 8 in 76% yield. Reductive cleavage of the benzyl group can generate the key chiral amine 9.

Scheme 1.

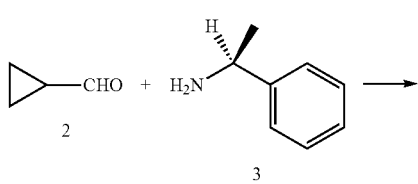

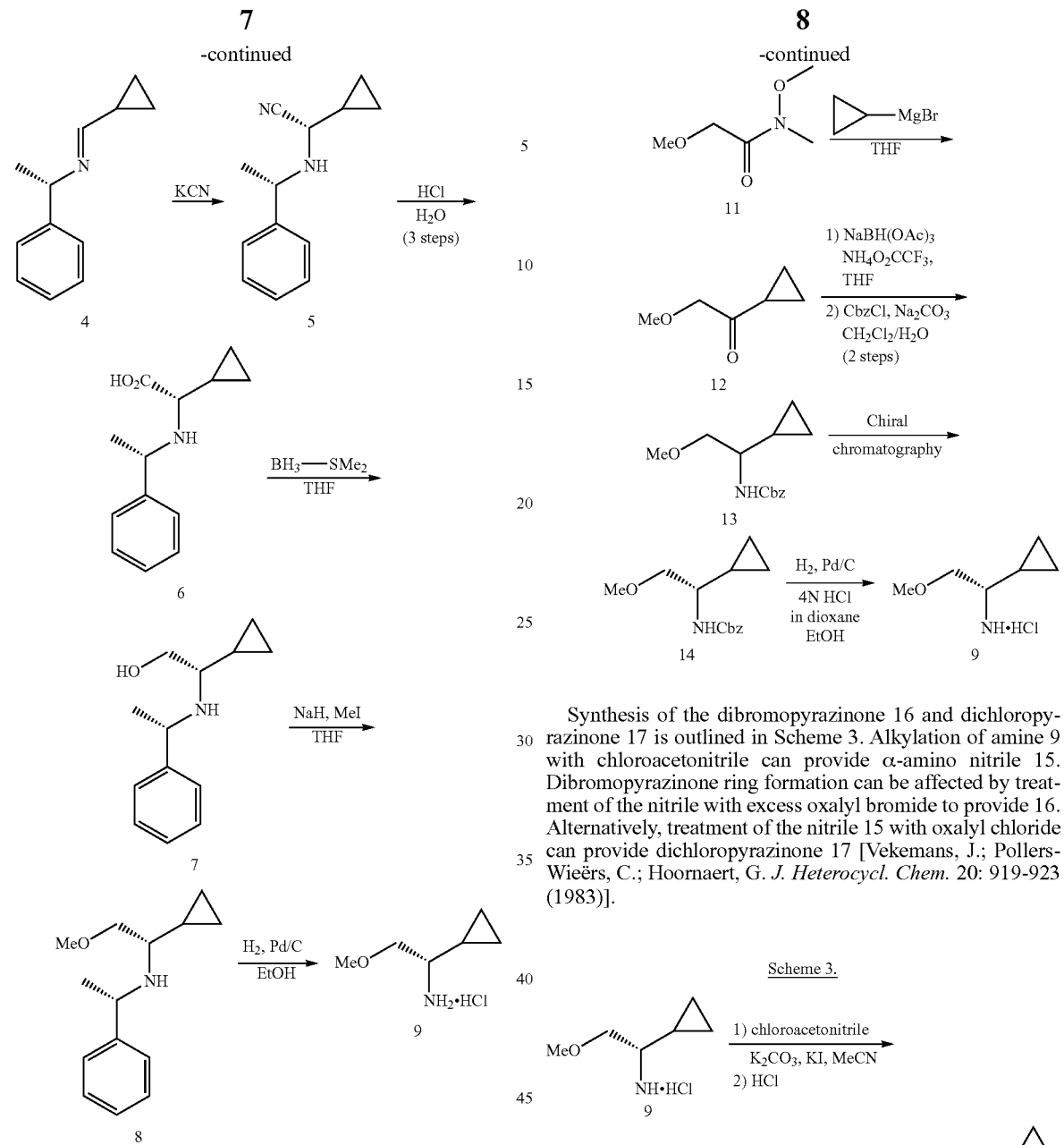

Synthesis of the dibromopyrazinone 16 and dichloropyrazinone 17 is outlined in Scheme 3. Alkylation of amine 9 with chloroacetonitrile can provide α-amino nitrile 15. Dibromopyrazinone ring formation can be affected by treatment of the nitrile with excess oxalyl bromide to provide 16. Alternatively, treatment of the nitrile 15 with oxalyl chloride can provide dichloropyrazinone 17 [Vekemans, J.; Pollers-Wieërs, C.; Hoornaert, G. *J. Heterocycl. Chem.* 20: 919-923 (1983)].

Route B to (S)-amine 9 begins with conversion of commercially available α-methoxy acid 10 to amide 11, followed by addition of cyclopropyl Grignard which can afford ketone 12. Reductive amination, followed by protection of the amine as the (benzyloxy)carbamate, can provide racemic intermediate 13. Separation of the enantiomers by chromatography can generate the single enantiomer 14. Deprotection under acidic conditions can provide (S)-amine 9.

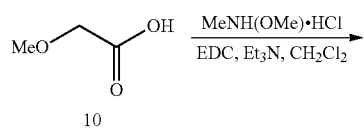

Synthesis of the pyridyl amine fragment 26 is shown in Schemes 4 and 5. Commercially available 2-amino-3-methylpyridine 18 can be nitrated by treatment with nitric acid and sulfuric acid using a modification of the two-step, one pot procedure of Hawkins and Roe [Hawkins, G. F.; Roe, A. *J. Org. Chem.* 14: 328-332 (1949)] to provide pyridone 19. Conversion to methoxypyridine 20 can be accomplished in high yield in a two-step procedure starting with treatment of 19 with POCl$_3$ followed by methanolysis. Installation of the 6-methyl substituent can be achieved through two different procedures, both involving vicarious nucleophilic aromatic substitution at the 6-position of nitropyridine 20. Method A involves generation of the anion of t-butyl chloroacetate, followed by hydrolysis of the resulting ester 21 to give the acid 22. Decarboxylation can be affected by heating under basic conditions in DMF to provide the 6-methylpyridine 23. Alternatively in Method B, the 6-methyl group can be installed directly by treatment of 20 with trimethylsulfoxonium iodide.

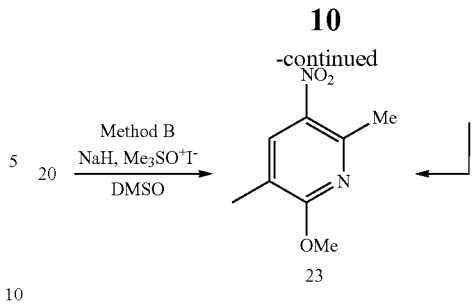

Completion of the synthesis of pyridyl amine 26 can be commenced by heating 23 under acidic conditions for 1-2 hours to furnish pyridone 24. The difluoromethyl ether 25 can be prepared by selective O-alkylation of 24 with difluorocarbene using, for example, the silyl ester of 2-fluorosulfonyldifluoroacetate (Dolbier, W. R.; Tian, F.; Duan, J. X.; Chen, Q. Y. *Org. Synth.* 2003, 80, 172-176; Dolbier, W. R.; Tian, F.; Duan, J. X.; Li, A.; Ait-Mohand, S.; Bautista, O.; Buathong, S.; Baker, J. M.; Crawford, J.; Anselme, P.; Cai, X. H.; Modzelewska, A.; Koroniak, H.; Battiste, M. A.; Chen, Q. Y. *J. Fluorine Chem.* 2004, 125, 459-469; Cai, X.; Zhai, Y.; Ghiviriga, I.; Abboud, K. A.; Dolbier, W. R. *J. Org. Chem.* 2004, 69, 4210-4215) or 2-fluorosulfonyldifluoroacetic acid (Chen, Q. Y.; Wu, S. W. *J. Fluorine Chem.* 1989, 44, 433-440). Final conversion to the pyridyl amine 26 can be accomplished by hydrogenation.

Scheme 4.

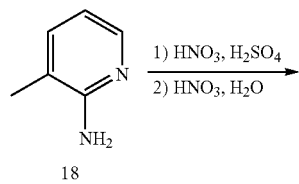

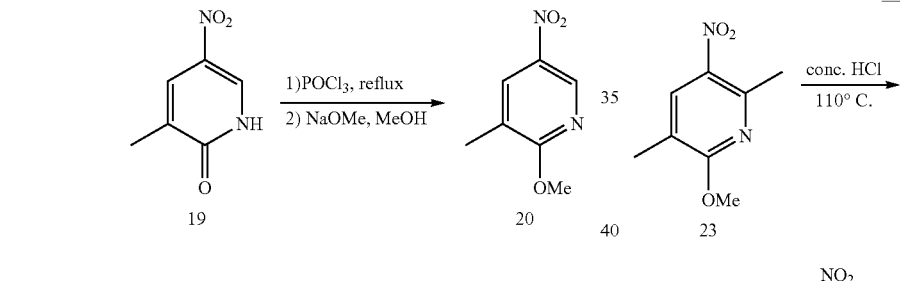

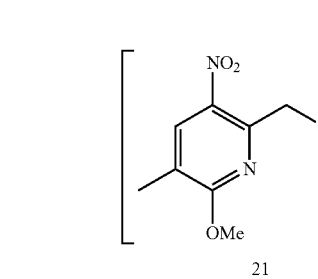

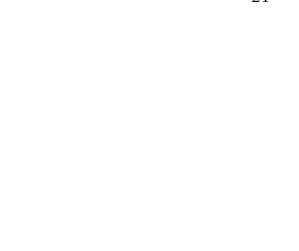

Scheme 5.

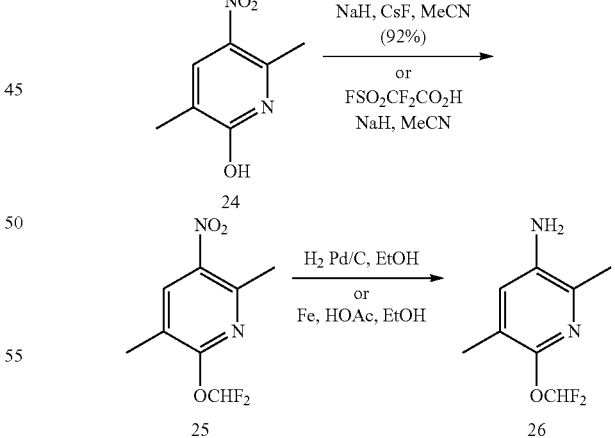

Completion of the synthesis of 1 is shown in Scheme 6. Coupling of the dibromopyrazinone 16 with pyridyl amine 26 can be achieved in the presence of NaHMDS to provide compound 26. Palladium-mediated coupling of 27 with zinc cyanide in DMF can provide cyanopyrazinone 1 [Maligres, P. E.; Waters, M. S.; Fleitz, F.; Askin, D. *Tetrahedron Lett.* 40: 8193-8195 (1999)].

Scheme 6.

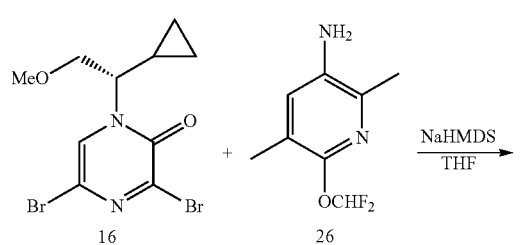

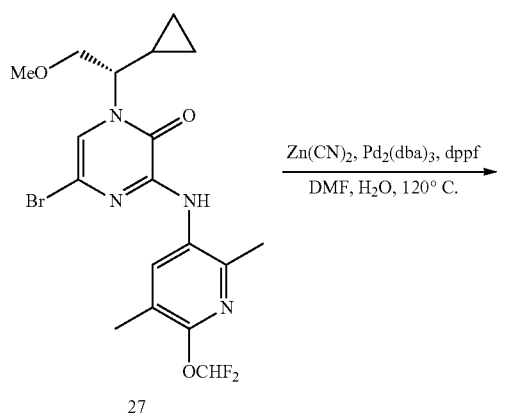

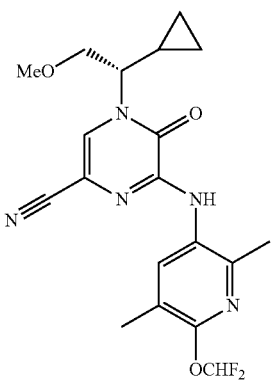

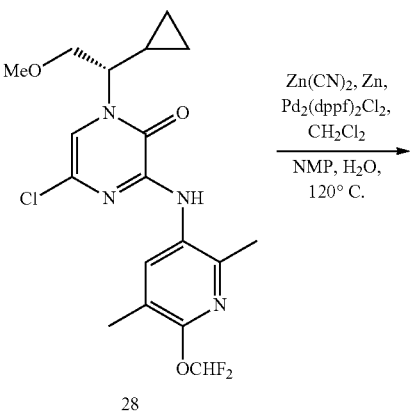

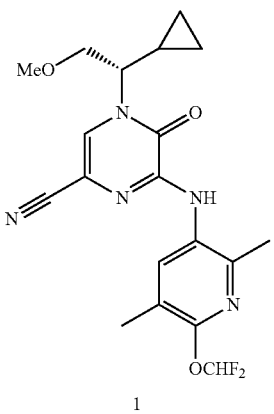

Alternatively, chloropyrazinone 29 can be converted to cyanopyrazinone 1 with zinc cyanide under palladium catalysis provided the 5-cyanopyrazinone 30. Demethylation of the methoxypyridine moiety can be effected by treatment with potassium iodide in acetic acid. Subsequent selective O-alkylation of the pyridinone with the trimethylsilyl ester of 2-fluorosulfonyldifluoroacetic acid can provide cyanopyrazinone 1.

Synthesis of cyanopyrazinone 1 from chloropyrazinone 28 can also be effected using zinc cyanide and palladium catalysis.

Scheme 7.

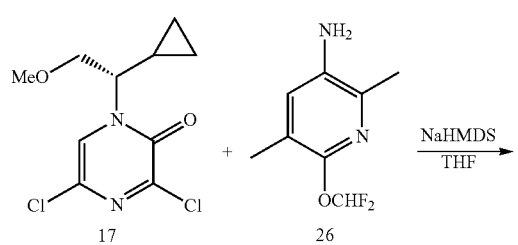

Scheme 8.

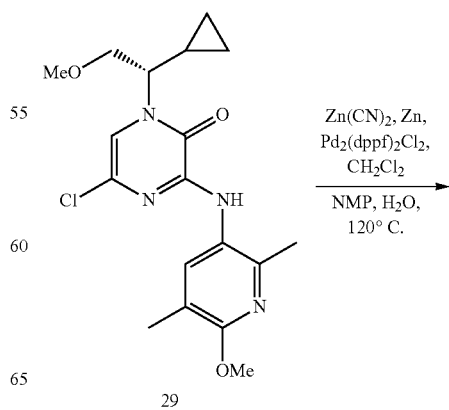

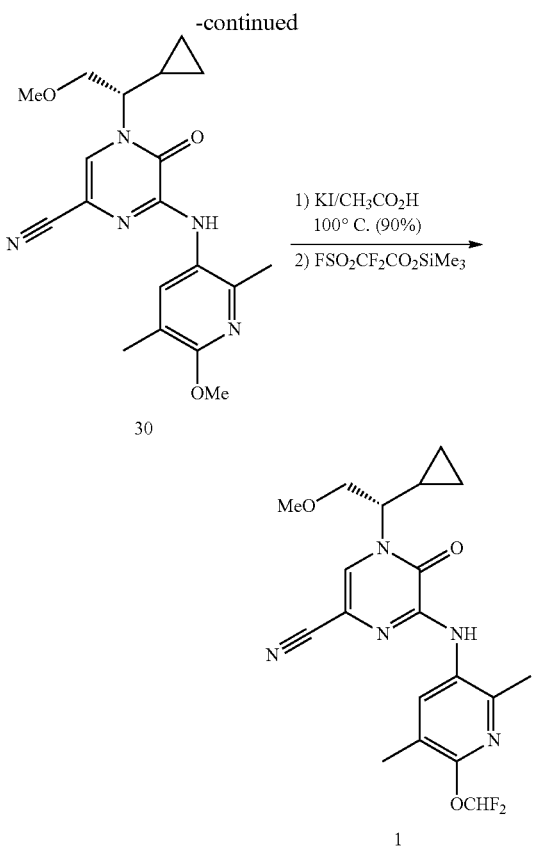

Biological Methods

CRF$_1$ Binding Assay. Frozen rat frontal cortex was thawed rapidly in assay buffer containing 50 mM Hepes (pH 7.0 at 23° C.), 10 mM MgCl$_2$, 2 mM EGTA, 1 μg/ml aprotinin, 1 μg/ml leupeptin, 1 μg/ml pepstatin A, 0.005% Triton X-100, 10 U/ml bacitracin and 0.1% ovalbumin and homogenized. The suspension was centrifuged at 32000×g for 30 minutes. The resulting supernatant was discarded and the pellet resuspended by homogenization in assay buffer and centrifuged again. The supernatant was discarded and the pellet resuspended by homogenization in assay buffer and frozen at −70° C. On the day of the experiment aliquots of the homogenate were thawed quickly and 25 μg/well added to 150 pM $^{125}$I-ovine-CRF ($^{125}$I-o-CRF) and drugs in a total volume of 100 μl assay buffer. The assay mixture was incubated for 2 hr at 21° C. Bound and free radioligand were then separated by rapid filtration using glass fiber filters (Whatman GF/B, pretreated with 0.3% PEI (polyethylenimine)) on a Brandel Cell Harvester. Filters were then washed multiple times with ice cold wash buffer (PBS w/o Ca$^{2+}$ and Mg$^{2+}$, 0.01% Triton X-100; pH 7.0 at 23° C.). Non-specific binding was defined using 1 μM DMP696, a CRF$_1$ selective antagonist [Li, Y-W. et al., CNS Drug Reviews 11: 21-52, (2005)]. Filters were then counted in a Wallac Wizard gamma counter. IC$_{50}$ values were determined in a five point (five drug concentrations) or ten point (ten drug concentrations) competition assay using non-linear regression by Microsoft Excel-fit.

CRF$_2$ Binding Assay. Frozen porcine choroid plexus was thawed rapidly in assay buffer containing 50 mM Hopes (pH 7.0 at 23° C.), 10 mM MgCl$_2$, 2 mM EGTA, 1 μg/ml aprotinin, 1 μg/ml leupeptin, 1 μg/ml pepstatin A, 0.005% Triton X-100, 10 U/ml bacitracin and 0.1% ovalbumin and homogenized. The suspension was centrifuged at 32000×g for 30 minutes. The resulting supernatant was discarded and the pellet resuspended by homogenization in assay buffer and centrifuged again. The supernatant was discarded and the pellet resuspended by homogenization in assay buffer and frozen at −70° C. On the day of the experiment aliquots of the homogenate were thawed quickly and 10 μg/well added to 100 pM $^{125}$I-sauvagine and drugs in a total volume of 100 μl assay buffer. The assay mixture was incubated for 2 hr at 21° C. Bound and free radioligand were then separated by rapid filtration using glass fiber filters (Whatman GF/B, pretreated with 0.3% PEI) on a Brandel Cell Harvester. Filters were then washed multiple times with ice cold wash buffer (PBS w/o Ca$^{2+}$ and Mg$^{2+}$, 0.01% Triton X-100 (pH 7.0 at 23° C.)). Non-specific binding was defined using 1 μM α-helical CRF (9-41). Filters were then counted in a Wallac Wizard gamma counter. IC$_{50}$ values were determined in a five point (five drug concentrations) competition assay using non-linear regression by Microsoft Excel-fit.

hCRF$_1$ Binding Assay. Membranes were prepared for binding using Y79 cells, a human retinoblastoma line that natively expresses human CRF$_1$ receptors [Hauger, R., et al., Journal of Neurochemistry 68: 2308-2316, (1997)]. Briefly, cells were grown and collected then the pellet homogenized in assay buffer containing 50 mM Hepes (pH 7.0 at 23° C.), 10 mM MgCl$_2$, 2 mM EGTA, 1 μg/ml aprotinin, 1 μg/ml leupeptin, 1 μg/ml pepstatin A, 0.005% Triton X-100, 10 U/ml bacitracin and 0.1% ovalbumin. The suspension was centrifuged at 32000×g for 30 minutes. The resulting supernatant was discarded and the pellet resuspended by homogenization in assay buffer and centrifuged again. The supernatant was discarded and the pellet resuspended by homogenization in assay buffer and aliquots frozen at −70° C. On the day of the experiment aliquots were thawed quickly and 25 μg/well added to 150 pM $^{125}$I-ovine-CRF and drugs in a total volume of 100 μl assay buffer. The assay mixture was incubated for 2 hr at 21° C. Bound and free radioligand were then separated by rapid filtration using glass fiber filters (Whatman GF/B, pretreated with 0.3% PEI) on a Brandel Cell Harvester. Filters were then washed multiple times with ice cold wash buffer (PBS w/o Ca$^{2+}$ and Mg$^{2+}$, 0.01% Triton X-100 (pH 7.0 at 23° C.)). Non-specific binding was defined using 1 μM DMP696. Filters were then counted in a Wallac Wizard gamma counter. IC$_{50}$ values were determined in a five point (five drug concentrations) competition assay using non-linear regression by Microsoft Excel-fit.

Binding Results. The primary screen to determine binding potency (IC$_{50}$ value) of (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile at the CRF$_1$ receptor was a competition binding experiment utilizing $^{125}$I-o-CRF as the labeled peptide ligand and rat frontal cortex membrane as the receptor source. (S)-4-(1-Cyclopropyl-2-methoxyethyl)-6-(6-(difluoromethoxy)-2,5-dimethylpyridin-3-ylamino)-5-oxo-4,5-dihydropyrazine-2-carbonitrile potently and completely inhibited $^{125}$I-o-CRF binding to rat frontal cortex membrane displaying an IC$_{50}$ of 0.86±0.04 nM (n=10) and a Hill Slope of 0.94±0.03 (n=10). These results include both 5 point and 10 point competition binding assays. For comparison DMP696, the well characterized small molecule selective CRF$_1$ antagonist, was also examined and displayed an IC$_{50}$ of 1.39±0.09 nM (n=10) and a Hill Slope of 1.00±0.02 (n=10). (S)-4-(1-Cyclopropyl-2-methoxyethyl)-6-(6-(difluoromethoxy)-2,5-dimethylpyridin-3-ylamino)-5-oxo-4,5-dihydropyrazine-2-carbonitrile also bound with high affinity to the native CRF$_1$ receptors present on the human retinoblastoma cell line Y79. (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile potently and completely inhibited $^{125}$I-o-CRF binding to Y79 membrane displaying an $IC_{50}$ of 1.81±0.46 nM (n=3). For comparison DMP696 was also examined and displayed an $IC_{50}$ of 1.71±0.53 nM (n=3). In contrast to its high affinity for the $CRF_1$ receptor, (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile showed little or no affinity at the $CRF_2$ receptor expressed in porcine choroid plexus membrane. While α-helical CRF (a truncated high affinity antagonist of $CRF_1$ and $CRF_2$ receptors) bound with high affinity to the $CRF_2$ receptors endogenously expressed on the porcine choroid plexus membrane ($IC_{50}$=25.7±2.9 nM, n=3), (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile displayed an $IC_{50}$>10,000 nM (n=3).

Situational Anxiety Behavioral Studies in Rats. (S)-4-(1-Cyclopropyl-2-methoxyethyl)-6-(6-(difluoromethoxy)-2,5-dimethylpyridin-3-ylamino)-5-oxo-4,5-dihydropyrazine-2-carbonitrile has been evaluated in a situational anxiety model to evaluate its anxiolytic potential. In this model, rats are placed in a small, darkened chamber located in an unfamiliar open field. Vehicle-treated rats spend most of the time within the chamber, consistent with a heightened state of anxiety [Takahashi L. K. et al, *Behav. Neurosci.* 103: 648-654, (1989)]. This model is sensitive to anxiolytics, including benzodiazepines such as chlordiazepoxide [Yang X-M. et al, *J. Pharmacol. Exp. Ther.* 255: 1064-1070, (1990)]. In addition, previous $CRF_1$ antagonists, such as DMP696 and DMP904 [McElroy J. F. et al., *Psychopharmacology* 165: 86-92, (2002); Lelas S. et al., *J. Pharmacol. Exp. Ther.* 309: 293-302, (2004)] were effective this model. The effects of (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile were compared with those of anxiolytic standards chlordiazepoxide (Librium®) and diazepam (Valium®) in this model. Male Sprague-Dawley rats weighing 180-300 g were purchased from Charles River Laboratories (Wilmington, Mass.). The rats were housed individually in suspended wire cages in colony rooms maintained at a constant temperature (21±2° C.) and humidity (50±10%). The rooms were illuminated 12 hours per day. The rats had ad libitum access to food and water throughout the studies. Behavioral studies were conducted between 0600 and 1300 h. Animals were maintained in accordance with the guidelines of the Animal Care and Use Committee of the Bristol-Myers Squibb Company, the "Guide for Care and Use of Laboratory Animals" (Institute of Animal Laboratory Resources, 1996), and the guidelines published in the National Institutes of Health Guide for the Care and Use of Laboratory Animals. Research protocols were approved by the Bristol-Myers Squibb Company Animal Care and Use Committee. All compounds were prepared in 0.25% methylcellulose and administered PO. Chlordiazepoxide, diazepam, and desipramine were purchased from Sigma Chemical Company. (S)-4-(1-Cyclopropyl-2-methoxyethyl)-6-(6-(difluoromethoxy)-2,5-dimethylpyridin-3-ylamino)-5-oxo-4,5-dihydropyrazine-2-carbonitrile was dosed in the volume of 2 ml/kg. All standards were dosed in the volume of 2 ml/kg. For all tests, data were analyzed by analysis of variance, followed by Dunnett's t-tests for individual comparisons. The significance value was set at 0.05. The data are presented in the text and figures as mean±standard error of the mean (SEM). Male Sprague-Dawley rats were habituated to handling and dosing the day before testing. On the day of testing, all compounds were administered PO by gavage 60 minutes before behavioral testing. To initiate testing, each animal was placed in a small galvanized steel cylinder (14 cm length, 10 cm diameter), which was placed lengthwise against one wall of an illuminated open field (106 cm length×92 cm width×50 cm height). The open field was illuminated by a 60-W incandescent bulb and illumination was titrated by a powerstat transformer to a 30-lux reading at the entrance to the cylinder. Behavior was assessed for 15 minutes by a trained observer unaware of treatment assignment. The latency of the animal to exit the cylinder, defined by the placement of all four paws into the open field, and explore the open field was recorded (in seconds). If the animal did not leave the cylinder after 15 minutes the trial was terminated and a score of 900 seconds was recorded. The Plexiglas chamber and the cylinder were cleaned with 1.0% glacial acetic acid between animals to prevent olfactory cues from influencing the behavior of subsequently tested animals. Following behavioral testing, animals were sacrificed and plasma samples and brains were taken for analysis of plasma exposure and central receptor occupancy.

Situational Anxiety Behavioral Studies Results. Vehicle-treated animals showed long latencies to exit the dark chamber and explore the open field. The mean exit latencies were 792±108 and 794±106 s in the chlordiazepoxide and diazepam studies, respectively (88% of the total test duration of 900 s for both studies). The benzodiazepine anxiolytics chlordiazepoxide and diazepam both dose-dependently decreased exit latency [chlordiazepoxide F(5.47)=7.62, p<0.0001; diazepam F(4.38)=15.17, p<0.0001]. The lowest effective dose of chlordiazepoxide (3.0 mg/kg, PO) decreased exit latency by 58% relative to vehicle-treated controls. Higher doses of chlordiazepoxide tested (10, 30, and 100 mg/kg, PO) also significantly decreased exit latency, by 97%, 72%, and 54%, respectively, relative to vehicle-treated animals. The U-shaped curve for these effects of chlordiazepoxide is probably due to the sedative properties of this drug. The lowest effective dose of diazepam (1.0 mg/kg, PO) decreased exit latency by 62% relative to control, and the higher doses tested (3.0 and 10 mg/kg, PO) further decreased exit latency by 69% and 91%, respectively, relative to vehicle-treated controls.

(S)-4-(1-Cyclopropyl-2-methoxyethyl)-6-(6-(difluoromethoxy)-2,5-dimethylpyridin-3-ylamino)-5-oxo-4,5-dihydropyrazine-2-carbonitrile was tested at single doses (1.0, 1.8, and 3.0 mg/kg, PO) in three separate studies, followed by a complete dose-response (0.56-3.0 mg/kg, PO) study. In all single-dose studies, vehicle-treated animals showed long latencies to exit the dark chamber and explore the open field. The mean exit latencies were 780±81, 748±77, and 824±76 s in the three studies, respectively (87%, 83%, and 92%, respectively, of the total test duration of 900 s). The positive control DMP696 (10 mg/kg), another $CRF_1$ receptor antagonist, significantly reduced exit latency in each of the three studies (decrease of 57%, 74%, and 81%, respectively). The doses of 1.8 and 3.0 mg/kg, but not of 1.0 mg/kg, of (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile significantly decreased exit latency. The dose of 1.8 mg/kg reduced exit latency by 53% [F(2.23)=7.52, p=0.003] and the dose of 3.0 mg/kg by 51% [F(2.23)=14.05, p=0.0001].

In the dose-response study, vehicle-treated animals showed an exit latency of 747±78 s (83% of the total test duration of 900 s). The positive control, DMP696 at 10 mg/kg, significantly reduced exit latency (62% decrease). Consistent with the effects shown in the single-dose studies, (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile dose-dependently reduced exit latency in the situational anxiety model when administered orally [$F(5.47)=3.69$, $p=0.007$]. The lowest effective dose of (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile was 1.8 mg/kg, which resulted in a decrease in exit latency of 60% relative to vehicle-treated controls. A higher dose of (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile (3.0 mg/kg) also significantly decreased exit latency by 56%. Lower doses of (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile (0.56 and 1.0 mg/kg) did not significantly alter exit latency. In summary, (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile showed comparable potency to the benzodiazepines diazepam and chlordiazepoxide in producing anxiolytic-like effects in the rat situational anxiety model.

Pharmaceutical Composition and Methods of Use

Compound I demonstrates inhibition of CRF. Inhibition of CRF correlates with efficacy for psychiatric disorders and neurological diseases including depression, anxiety related disorders, irritable bowel syndrome, addiction and negative aspects of drug and alcohol withdrawal, and other conditions associated with CRF. As such, Compound I can be useful for the treatment of these disorders and other aspects of the invention are compositions and methods of using Compound I to treat these conditions and other conditions associated with aberrant levels of CRF.

Another aspect of the invention is a method for the treatment of psychiatric or neurological conditions associated with CRF which comprises administering a therapeutically effective amount of (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile to a patient.

Another aspect of the invention is a method for the treatment of depression.

Another aspect of the invention is a method for the treatment of anxiety or an anxiety related disorder.

Another aspect of the invention is a method for the treatment of irritable bowel syndrome.

Another aspect of the invention is a method for the treatment of addiction or negative aspects of drug and alcohol withdrawal.

Compound I is generally given as a pharmaceutical composition comprised of a therapeutically effective amount of Compound I, or a pharmaceutically acceptable salt, and a pharmaceutically acceptable carrier and may contain conventional excipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 1 mg, 10 mg, 100 mg, 250 mg, 500 mg, and 1000 mg. Liquid compositions are generally in a unit dosage range of 1-100 mg/mL. Some examples of liquid dosage units are 1 mg/mL, 10 mg/mL, 25 mg/mL, 50 mg/mL, and 100 mg/mL.

The invention encompasses all conventional modes of administration; oral and parenteral methods are preferred. Typically, the daily dose will be 0.01-100 mg/kg body weight daily. Generally, more compound is required orally and less parenterally. The specific dosing regime, however, should be determined by a physician using sound medical judgement.

DESCRIPTION OF THE SPECIFIC EMBODIMENTS

In the following examples, all temperatures are given in degrees Centigrade. Melting points were recorded on a Meltemp 3.0 Laboratory Devices, Inc. or Thomas Scientific Unimelt capillary melting point apparatus and are uncorrected. Proton magnetic resonance ($^1$H NMR) spectra were recorded on a Bruker 400 or a Bruker 500 MHz spectrometer. All spectra were determined in the solvents indicated and chemical shifts are reported in $\delta$ units downfield from the internal standard tetramethylsilane (TMS) and interproton coupling constants are reported in Hertz (Hz). Multiplicity patterns are designated as follows: s, singlet; d, doublet; t, triplet; q, quartet; m, multiplet; br, broad peak; dd, doublet of doublet; br d, broad doublet; dt, doublet of triplet; br s, broad singlet; dq, doublet of quartet. Optical rotations ROD were determined on a Rudolph Scientific Autopol IV polarimeter in the solvents indicated; concentrations are given in mg/mL. Low resolution mass spectra (MS) and the apparent molecular (M+H$^+$) or (M−H)$^+$ was determined on a Finnegan SSQ7000. High resolution mass spectra were determined on a Finnegan MAT900. Liquid chromatography (LC)/mass spectra were run on a Shimadzu LC coupled to a Water Micromass ZQ.

Abbreviations generally follow convention terms used in the art: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "$\delta$" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

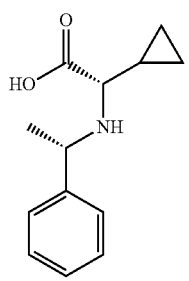 [SMILES: C[C@H](N[C@H](C(=O)O)C1CC1)c1ccccc1]

(S)-2-Cyclopropyl-2-[(S)-1-phenylethylamino]acetic acid. A stirred solution of cyclopropane carboxaldehyde (200.0 g, 1.42 mol) and S-(−)-1-phenyl ethylamine (172.9 g, 1.42 mol) in methanol (2.0 L) in a 3-neck 5 L round bottom flask was heated at 75° C. for 2 h. The reaction mixture was then cooled to room temperature and potassium cyanide (185.0 g, 1.42 mol) was added in portions. The reaction mixture was stirred overnight at room temperature. Water (600 mL) was added followed by dropwise addition of conc. HCl (250 mL) until the reaction mixture reached pH 9-10. The mixture was then extracted with ethyl acetate (4×1 L) and the combined organic layers were concentrated under reduced pressure to afford a yellow oil. Conc. HCl (3.5 L) was added to this residue and the mixture was heated at 95° C. overnight. After cooling to room temperature, 10% potassium hydroxide solution was added dropwise with cooling and stirring until the pH was nearly neutral (pH 7-8). Stirring was continued for an additional 45 min at 0° C. The contents was filtered and washed thoroughly with cold methanol (5 L). The moisture content at this stage was observed to be about 8-10%. The solid was re-suspended in dry acetone (7 L) and filtered to obtain (S)-2-cyclopropyl-2-[(S)-1-phenylethylamino]acetic acid (330 g, 52% yield) as a solid with <1% moisture: $^1$H NMR (400 MHz, DMSO-$d_6$) δ 7.44-7.26 (m, 5H), 3.91-3.86 (m, 1H), 2.28-2.22 (m, 1H), 1.34 (d, J=4.0 Hz, 3H), 0.93-0.89 (m, 1H), 0.41-0.37 (m, 2H), 0.31-0.27 (m, 1H), 0.11-0.07 (m, 1H).

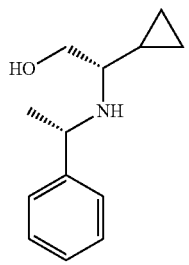

(S)-2-Cyclopropyl-2-[(S)-1-phenylethylamino]ethanol. To a solution of (S)-2-cyclopropyl-2-[(S)-1-phenylethylamino]acetic acid (400 g, 1.82 mol) in dry THF (5.2 L) at 0° C. was added borane dimethylsulfide (neat) (485 g, 6.39 mol) with vigorous stirring. The reaction mixture was stirred overnight at room temperature. Reaction progress was monitored by HPLC. Stirring was continued until the acid was consumed completely (18-20 h). Upon completion the reaction mixture was cooled to 0° C. and methanol (6 L) was added dropwise. The mixture was concentrated under vacuum and the residue was dissolved in chloroform (5 L). The organic layer was washed with 10% aqueous NaHCO$_3$ solution (2×1 L) followed by brine, dried over Na$_2$SO$_4$, filtered and concentrated to afford a tan-yellow oil. The oil was distilled under reduced pressure to afford (S)-2-cyclopropyl-2-[(S)-1-phenylethylamino]ethanol (166 g, 44% yield) as a colorless oil: by 175-184° C., 0.1 mm Hg; [α]$^{25}_D$ −52.1 (c 1.0, CHCl$_3$); $^1$H NMR (400 MHz, CDCl$_3$) δ $^1$H NMR (400 MHz, CDCl$_3$) δ 7.33-7.20 (m, 5H), 3.91-3.86 (m, 1H), 3.67 (dd, $J_{AB}$=10.6, $J_{AX}$=3.8 Hz, 1H), 3.39 (dd, $J_{BA}$=10.6, $J_{BX}$=4.3 Hz, 1H), 2.40 (s br, 2H), 1.70-1.65 (m, 1H), 1.35 (d, J=6.6 Hz, 3H), 0.88-0.82 (m, 1H), 0.47-0.37 (m, 2H), 0.05--0.06 (m, 2H); $^{13}$C NMR (100 MHz, DMSO-$d_6$) δ 146.8, 127.6, 126.2, 125.9, 63.0, 60.5, 54.4, 24.4, 13.3, 3.0, 1.5; LRMS (ESI) m/e 206.3 [(M+H)$^+$, calcd for C$_{13}$H$_{20}$NO 206.2].

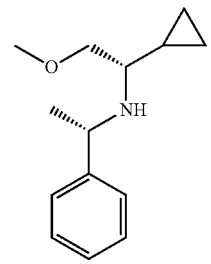 [SMILES: COC[C@@H](N[C@@H](C)c1ccccc1)C1CC1]

(S)-1-Cyclopropyl-2-methoxy-N—[(S)-1-phenylethyl]ethanamine. To a solution of (S)-2-cyclopropyl-2-[(S)-1-phenylethylamino]ethanol (29.2 g, 0.143 mol) in THF (700 mL) at 0° C. was added NaH (6.29 g, 0.157 mol, 60% dispersion in mineral oil). The cooling bath was removed and the reaction mixture was allowed to warm to room temperature and was stirred at room temperature for 30 min. Methyl iodide (20.30 g, 0.143 mol) was then added dropwise via syringe. Some warming occurred soon after the addition was complete. The temperature of the reaction mixture was controlled at ~25° C. with a water bath containing a small amount of ice. The reaction mixture was stirred at room temperature for 4 h. The reaction mixture was then slowly quenched with saturated aqueous NaHCO$_3$ solution and was transferred to a separatory funnel containing saturated aqueous NaHCO$_3$ solution (400 mL). The aqueous layer was extracted with ethyl acetate (3×300 mL). The combined organic layers were washed with brine, dried over MgSO$_4$, filtered and concentrated. The crude product was purified by column chromatography on silica gel (5% MeOH in 1:1 ethyl acetate/hexanes) to afford (5)-1-cyclopropyl-2-methoxy-N-[(S)-1-phenylethyl]-ethanamine (26.52 g, 85% yield) as a light brown oil: [α]$^{25}_D$ −61.5 (c 0.72, CHCl$_3$); $^1$H NMR (400 MHz, CDCl$_3$) δ 7.30-7.25 (m, 4H), 7.20-7.16 (m, 1H), 3.98-3.93 (q, J=6.8 Hz, 1H), 3.50 (dd, $J_{AB}$=9.5, $J_{AX}$=3.5 Hz, 1H), 3.35 (s, 3H), 3.34 (dd, $J_{BA}$=9.5, $J_{BX}$=5.8 Hz, 1H), 1.79-1.74 (m, 2H), 1.33 (d, 6.5 Hz, 3H), 0.73-0.67 (m, 1H), 0.36-0.34 (m, 2H), 0.03--0.06 (m, 2H); GC/MS (ESI) m/e 220.2 [(M+H)$^+$, calcd for C$_{14}$H$_{22}$NO 220.2].

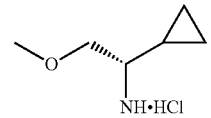

(S)-1-Cyclopropyl-2-methoxyethanamine hydrochloride. (S)-1-cyclopropyl-2-methoxy-N—[(S)-1-phenylethyl]ethanamine (100 g, 458 mmol) was combined with Pd(OH)$_2$/C (50 g, 20% on carbon) and ethanol (1.2 L) in a Parr bottle. The reaction mixture was placed under an H$_2$ atmosphere (15 psi) and was shaken for 18 h. The reaction mixture was then filtered through a pad of Celite into a flask containing 2 N HCl in Et$_2$O (360 mL) with stirring. The resulting filtrate was concentrated to a yellow solid, which was then co-evaporated with Et$_2$O (500 mL). The resulting solid was dried overnight in vacuo to give (S)-1-cyclopropyl-2-methoxyethanamine hydrochloride (69 g, 99% yield) as a white solid: mp 190-192° C.; [α]$^{25}_D$ +16.3 (c 0.446, MeOH); $^1$H NMR (400 MHz, CDCl$_3$) δ 8.41 (s br, 3H), 3.68 (d, J=5.6 Hz, 2H), 3.39 (s, 3H), 2.64-2.60 (m, 1H), 1.20-1.13 (m, 1H), 0.71-0.58 (m, 3H), 0.32-0.28 (m, 1H); $^{13}$C NMR (100 MHz, CDCl$_3$) δ 72.1, 59.2, 57.5, 10.7, 4.2, 4.1; LRMS (ESI) m/e 231.2 [(2M+H)$^+$, calcd for C$_{12}$H$_{27}$N$_2$O$_2$ 231.2].

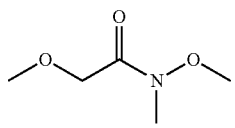

N,2-Dimethoxy-N-methylacetamide. Triethylamine (115 mL) was added to a solution of methoxyacetic acid (35.0 g, 389 mmol) in CH$_2$Cl$_2$ (1200 mL) at room temperature. N,O-dimethylhydroxylamine hydrochloride (45.5 g, 467 mmol) was added, and after stirring for 5 min, the suspension was cooled to 0° C. Ethyl diazocarboxylate (EDC) (81.7 g, 428 mmol) was then added and the reaction mixture was stirred overnight while allowing it to warm to room temperature. The mixture was poured into a separatory funnel and diluted with CH$_2$Cl$_2$ (500 mL). The organic layer was washed with 1 N HCl (2×300 mL), saturated aqueous NaHCO$_3$ solution (2×300 mL), and brine (300 mL), The resulting solution was dried over MgSO$_4$, filtered and concentrated in vacuo. The product was purified by column chromatography on a short column of silica gel (5% methanol in CH$_2$Cl$_2$) to afford N,2-dimethoxy-N-methylacetamide (33.2 g, 64% yield) as a colorless oil: $^1$H NMR (400 MHz, CDCl$_3$) δ 4.20 (s, 2H), 3.67 (s, 3H), 3.45 (s, 3H), 3.17 (s, 3H); $^{13}$C NMR (100 MHz, CDCl$_3$) δ 173.0, 69.7, 69.4, 61.4, 59.4; LRMS (ESI) m/e 134.1 [(M+H)$^+$, calcd for C$_5$H$_{12}$NO$_3$ 134.1].

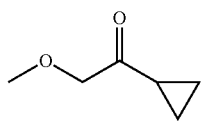

1-Cyclopropyl-2-methoxyethanone. Magnesium turnings (15.2 g, 632 mmol) were added to a 5-L 3-necked flask equipped with an addition funnel. The flask, funnel, and turnings were flame dried and then a reflux condenser was then placed on the flask. After the flask and contents had cooled to room temperature, diethyl ether (100 mL) was added to the flask, followed by addition of a portion of cyclopropyl bromide (5.0 mL, 7.55 g, 62.4 mmol) and several crystals of iodine. After the reaction had initiated, diethyl ether (400 mL) was added to the reaction flask. The remaining cyclopropyl bromide (87.3 g, 721 mmol) was then added slowly over 30 min with intermittent cooling of the reaction mixture with an ice-water bath. After the addition was complete and the magnesium was consumed, additional diethyl ether (700 mL) was added and the reaction mixture was cooled to 0° C. The magnetic stirrer was replaced with a mechanical stirrer and a solution of N,2-dimethoxy-N-methylacetamide (42.07 g, 316 mmol) dissolved in diethyl ether (500 mL) was added slowly over 30 min via the addition funnel. A white solid formed during this time. After the addition was complete, the cooling bath was removed and the mixture was stirred at room temperature for 1 h. The mixture was then cooled to 0° C. and the reaction was quenched by the addition of 1 N HCl (700 mL, added slowly at first). After stirring for an additional 15 min, the mixture was transferred to a separatory funnel, and the aqueous layer was extracted with ether (3×500 mL). The combined organic layers were washed with saturated aqueous NaHCO$_3$ solution (400 mL), brine (400 mL), dried over MgSO$_4$, filtered and concentrated with minimal vacuum (500 mbar). The product was purified by distillation under reduced pressure while submerging the collection flask in a dry ice/isopropanol bath to afford 1-cyclopropyl-2-methoxyethanone (29.2 g, 81% yield) as a colorless oil: by 35-38° C., 5 mm Hg; $^1$H NMR (400 MHz, CDCl$_3$) δ 4.13 (s, 2H), 3.43 (s, 3H), 2.11-2.07 (m, 1H), 1.10-1.06 (m, 2H), 0.94-0.89 (m, 2H); GC/MS (CI) m/e 115.1 [(M+H)$^+$, calcd for C$_6$H$_{11}$O$_2$ 115.1].

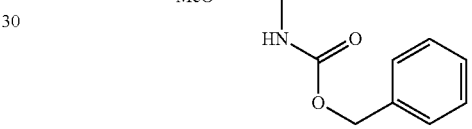

Benzyl 1-cyclopropyl-2-methoxyethylcarbamate. 1-Cyclopropyl-2-methoxyethanone (10.0 g, 88.0 mmol) in THF (1000 mL) was treated with ammonium trifluoroacetate (115 g, 880 mmol) and the mixture was cooled to 0° C. Sodium triacetoxyborohydride (27.9 g, 133 mmol) was added, the cooling bath was removed and the reaction mixture was gently heated at 40° C. with a warm water bath for 2 h. The mixture was cooled to room temperature and concentrated to give 1-cyclopropyl-2-methoxyethanamine which was used directly in the next step.

Crude 1-cyclopropyl-2-methoxyethanamine from the previous step was dissolved in CH$_2$Cl$_2$/H$_2$O (300 mL/300 mL) and Na$_2$CO$_3$ (111.9 g, 1.06 mol) was added. The reaction mixture was placed in an ice bath and CbzCl (16.46 g, 96.78 mmol) was added via syringe. During the addition, the internal reaction mixture temperature was maintained at 15-20° C. After the addition was complete, the reaction mixture was stirred at room temperature for 2 h. The mixture was poured into a separatory funnel, diluted with H$_2$O, (300 mL), and extracted with CH$_2$Cl$_2$ (3×300 mL). The combined organic layers were washed with brine (300 mL), dried over MgSO$_4$, filtered and concentrated. The product was purified by column chromatography on silica gel (30% ethyl acetate in hexanes) to furnish benzyl 1-cyclopropyl-2-methoxyethylcarbamate (17.2 g, 78% yield for 2 steps) as an oil which crystallized upon standing: mp 190.5-192° C.; $^1$H NMR (400 MHz, DMSO-d$_6$) δ 7.39-7.29 (m, 5H), 7.17 (d, J=8.5 Hz, 1H), 5.00 (s, 2H), 3.36-3.34 (m, 2H), 3.23 (s, 3H), 3.19-3.14 (m, 1H), 0.85-0.79 (m, 1H), 0.43-0.37 (m, 1H), 0.35-0.22 (m, 2H), 0.20-0.16 (m, 1H); LRMS (ESI) mile 250.3 [(M+H)$^+$, calcd for C$_{14}$H$_{20}$NO$_3$ 250.1].

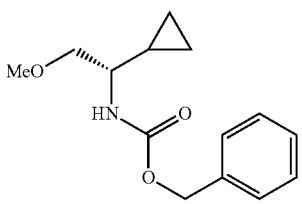 [SMILES: COC[C@@H](NC(=O)OCc1ccccc1)C1CC1]

(S)-Benzyl-cyclopropyl-2-methoxyethylcarbamate. Racemic 1-cyclopropyl-2-methoxyethylcarbamate was separated into its enantiomers by HPLC: Chiralpak AD column (10 cm×50 cm), 94% heptane/6% ethanol, 300 mL/min, λ=210 nm, 1 gram per injection, 30 min method, Peak 1 (S), Peak 2 (R) and was determined to have an optical purity >99% ee by analytical HPLC (Chiralpak AD column, 4.6×250 mm, 95% heptane/5% ethanol, 0.8 mL/min, λ=212 nm, $t_R$=15.79 min): mp 190.5-192° C.; $[\alpha]^{25}_D$ −18.2 (c 0.500, $CHCl_3$); $^1$H NMR (400 MHz, DMSO-$d_6$) δ 7.39-7.29 (m, 5H), 7.17 (d, J=8.5 Hz, 1H), 5.00 (s, 2H), 3.36-3.34 (m, 2H), 3.23 (s, 3H), 3.19-3.14 (m, 1H), 0.85-0.79 (m, 1H), 0.43-0.37 (m, 1H), 0.35-0.22 (m, 2H), 0.20-0.16 (m, 1H); $^{13}$C NMR (100 MHz, $CDCl_3$) δ 155.6, 136.9, 128.0, 127.38, 127.34, 74.0, 64.8, 57.8, 53.5, 12.6, 2.2, 1.5; LRMS (ES$^+$) m/e 272.3 [(M+Na)$^+$, calcd for $C_{14}H_{19}NO_3Na$ 272.1].

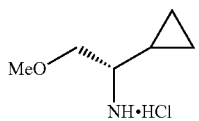

(S)-1-cyclopropyl-2-methoxyethanamine hydrochloride. To a solution of (S)-1-cyclopropyl-2-methoxyethylcarbamate (4.36 g, 17.5 mmol) in EtOH (80 mL) and $CHCl_3$ (3 mL) in a Parr bottle was added 4 N HCl in dioxane (5 mL) and Pd/C (476 mg, 10%, wet, Degussa type). The mixture was placed on a Parr shaker under $H_2$ atm at 45 psi for 16 h. The reaction mixture was filtered through a pad of Celite and the filtrate was concentrated then reconcentrated from hexanes (2×) to afford (S)-1-cyclopropyl-2-methoxyethanamine hydrochloride (2.65 g, 100% yield) as a white solid: mp 190-192° C.; $[\alpha]^{25}_D$ +14.3 (c 0.446, MeOH); $^1$H NMR (400 MHz, $CDCl_3$) δ 8.41 (s br, 3H), 3.68 (d, J=5.6 Hz, 2H), 3.39 (s, 3H), 2.64-2.60 (m, 1H), 1.20-1.13 (m, 1H), 0.71-0.58 (m, 3H), 0.32-0.28 (m, 1H); $^{13}$C NMR (100 MHz, $CDCl_3$) δ 72.1, 59.2, 57.5, 10.7, 4.2, 4.1; LRMS (ESI) m/e 231.2 [(2M+H)$^+$, calcd for $C_{12}H_{27}N_2O_2$ 231.2].

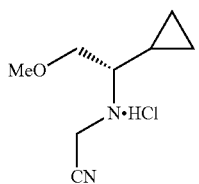

(S)-2-(1-Cyclopropyl-2-methoxyethylamino)acetonitrile hydrochloride. Chloroacetonitrile (8.40 mL, 133 mmol) was added to a stirred suspension of (S)-1-cyclopropyl-2-methoxyethanamine hydrochloride (20.0 g, 133 mmol), $K_2CO_3$ (52.0 g, 376 mmol) and KI (24.2 g, 145 mmol) in acetonitrile (300 mL) at room temperature. The mixture was stirred at 48° C. for 17 hours. The reaction mixture was then cooled to room temperature then filtered through a pad of Celite. The resulting filtrate was concentrated to a dark brown semi-solid. The solid was suspended in $CH_2Cl_2$ and purified by column chromatography on silica gel ($CH_2Cl_2$→3% methanol in $CH_2Cl_2$) to yield a brown oil (18.8 g). The oil was dissolved in $Et_2O$ (150 mL) and the solution was acidified with 2 N HCl in $Et_2O$ (100 mL) to give (S)-2-(1-cyclopropyl-2-methoxyethylamino)-acetonitrile hydrochloride (23.6 g, 93% yield) as an off-white solid: $[\alpha]^{25}_D$ +22.9 (c 0.714, $CHCl_3$); $^1$H NMR (400 MHz, $CDCl_3$) δ 10.51 (s br, 2H), 4.39 (ABq, $J_{AB}$=16.7, Δν=24.4 Hz, 2H), 3.94 (dd, $J_{AB}$=10.6, $J_{AX}$=7.8 Hz, 1H), 3.79 (dd, $J_{BA}$=10.8, $J_{BX}$=2.2 Hz, 1H), 3.42 (s, 3H), 2.79-2.75 (m, 1H), 1.25-1.17 (m, 1H), 0.90-0.83 (m, 1H), 0.78-0.70 (m, 2H), 0.39-0.34 (m, 1H); LRMS (ES$^+$) m/e 155.2 [(M+H)$^+$, calcd for $C_8H_{15}N_2O$ 155.1].

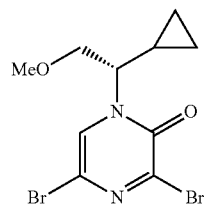

(S)-3,5-Dibromo-1-(1-cyclopropyl-2-methoxyethyl) pyrazin-2(1H)-one. (S)-2-(1-cyclopropyl-2-methoxyethylamino)acetonitrile hydrochloride (15.0 g, 78.7 mmol) was suspended in anhydrous dichloromethane (300 mL) in a 1 L, 3-necked round bottom flask equipped with an addition funnel. The mixture was cooled to −60° C. and oxalyl bromide (41.3 mL, 440 mmol) was added dropwise over 15 min. After addition was complete, the cooling bath was removed and the reaction mixture was allowed to warm to room temperature and was then heated at 40° C. for 3 hours. The mixture was cooled to room temperature and concentrated under vacuum. The solid was purified by direct addition to the head of a silica gel column and eluted (5%→20% ethyl acetate in hexanes) after residual oxalyl bromide had stopped reacting with the silica gel to give (S)-3,5-dibromo-1-(1-cyclopropyl-2-methoxyethyl)pyrazin-2(1H)-one (15.5 g, 56% yield) as an off-white solid: mp 98.5-100.5° C.; $[\alpha]^{25}_D$ −71.8 (c 1.19, $CHCl_3$); $^1$H NMR (400 MHz, $CDCl_3$) δ 7.61 (s, 1H), 4.08-4.04 (m, 1H), 3.72 (dd, $J_{AB}$=10.5, $J_{AX}$=4.5 Hz, 1H), 3.61 (dd, $J_{BA}$=10.3, $J_{BX}$=3.0 Hz, 1H), 3.32 (s, 3H), 1.41-1.36 (m, 1H), 0.82-0.76 (m, 1H), 0.65-0.59 (m, 1H), 0.54-0.48 (m, 1H), 0.32-0.27 (m, 1H); LRMS (APCI) m/e 351.1 [(M+H)$^+$, calcd for $C_{10}H_{13}N_2O_2Br_2$ 350.9].

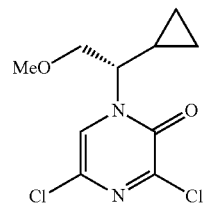 [SMILES: COC[C@H](C1CC1)n1cc(Cl)nc(Cl)c1=O]

(S)-3,5-Dichloro-1-(1-cyclopropyl-2-methoxyethyl) pyrazin-2(1H)-one. Oxalyl chloride (54.5 mL, 624 mmol) was added dropwise to a cold (<8° C.) solution of (S)-2-(1-cyclopropyl-2-methoxyethylamino)acetonitrile hydrochloride (23.6 g, 124 mmol) in 1,4 dioxane (300 mL) and methylene chloride (200 mL). The reaction mixture was then heated at 53° C. for 19 h. The reaction mixture was cooled to room temperature and concentrated to a semi-solid then co-evaporated three times with $CH_2Cl_2$ (50 mL). The resulting brown solid was purified by column chromatography on silica gel (0→10%→20% ethyl acetate in hexanes) to afford (S)-3,5-dichloro-1-(1-cyclopropyl-2-methoxyethyl)pyrazin-2 (1H)-one (22.4 g, 69% yield) as a white solid: mp 109.8-110.8° C.; $[\alpha]^{25}_D$ −88.8 (c 0.513, $CHCl_3$); $^1$H NMR (400 MHz, $CDCl_3$) δ 7.54 (s, 1H), 4.12-4.08 (m, 1H), 3.73 (dd, $J_{AB}$=10.3, $J_{AX}$=4.5 Hz, 1H), 3.62 (dd, $J_{BA}$=10.3, $J_{BX}$=3.0 Hz, 1H), 3.32 (s, 3H), 1.43-1.37 (m, 1H), 0.82-0.76 (m, 1H), 0.65-0.61 (m, 1H), 0.55-0.50 (m, 1H), 0.33-0.27 (m, 1H); LRMS (ESI) m/e 206.3 [(M+H)$^+$, calcd for $C_{10}H_{13}N_2O_2Cl_2$ 263.0]. Anal. calcd. for $C_{10}H_{12}N_2O_2Cl_2$: C, 45.64; H, 4.59; N, 10.64. Found: C, 45.74; H, 4.62; N, 10.61.

(S)-3,5-dichloro-1-(1-cyclopropyl-2-methoxyethyl) pyrazin-2(1H)-one [160 g, 90-95% of the (S)-enantiomer] from various batches was processed by Thar SFC to isolate the (S)-enantiomer in >99% enantiomeric purity. A total of 133 g of (S)-3,5-dichloro-1-(1-cyclopropyl-2-methoxyethyl) pyrazin-2(1H)-one was isolated in 3 batches. 11.8 g of the undesired isomer was also obtained. The enantiomeric excess (ee) of the compounds delivered were >99%. Preparative conditions on Thar 350 SFC were as follows: amount racemate (g): 65, 58, 37; column: Chiralpak AD-H, 5×25 cm; mobile phase: 10% EtOH in $CO_2$; pressure (bar): 100; flow rate (ml/min): 200; solution concentration (mg/ml): 50; injection amount (ml): 6; Cycle time (min/inj): 3.5; temperature: 35; throughput (g/hr): 5.1; Detector λ: 220.

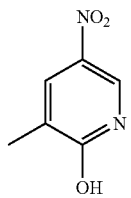

3-Methyl-5-nitropyridin-2-ol. A 3-necked, 2-L, round-bottomed flask equipped with a mechanical stirrer, an addition funnel and a thermometer was placed in an ice-water bath. Conc. $H_2SO_4$ (150 mL) was added to the flask. 2-Amino-3-methylpyridine (50.0 g, 0.463 mol, Lancaster, CAS 1603-40-3, mp. 29° C., prewarmed in a warm water bath to melt it) was weighed out in a 125 mL Erlenmeyer flask and was subsequently added in small portions via a prewarmed Pasteur pipet with the narrow tip broken off. The Erlenmeyer flask was kept in a warm water bath during the addition to prevent the starting material from solidifying. The temperature rose to ea. 45° C. during the addition and white smoke/fog formed within the flask. Conc. $H_2SO_4$ (100 mL) was added to the residual starting material and the mixture was added to the reaction flask. The resulting mixture was a milky-white suspension. A solution of conc. $H_2SO_4$ (35 mL) and 70% nitric acid (35 mL) was premixed with ice-water bath cooling and transferred into the addition funnel. After the internal temperature of the reaction mixture had cooled to 10-15° C. (but not below 10° C.), the premixed $H_2SO_4$/$HNO_3$ acid mixture was added dropwise at a rate such that the internal reaction temperature rose to 20-25° C. (5-10 min addition time). After the addition was complete, the ice-water bath was replaced with a tap-water bath. The reaction temperature slowly increased to ca. 30° C. range and then cooled down to room temperature. The reaction should be monitored during this time to ensure that the temperature does not rise too high. The reaction mixture was then stirred overnight and then 70% nitric acid (35 mL) was added dropwise via the addition funnel to the dark red-brown mixture at a rate of addition such that the temperature did not exceed 35° C. At this time, the reaction flask was sitting in a water bath containing water at room temperature. Water (500 mL) was then added to the reaction flask in portions via addition funnel. The first ca. 150 mL of water was added dropwise while allowing the internal temperature to climb slowly to 50-60° C. The rate of stirring was increased in order to break up any foaming that occurred. Brown gas evolved during the addition of the initial ca. 150 mL of water. The remaining ca. 350 mL of water was added at a faster rate after gas evolution had stopped and a temperature increase was no longer observed. The reaction turned from a dark cloudy brown to a clear orange solution. Some yellow precipitate may form as the reaction cools to below 50° C. The water bath was then removed, and replaced with a heating mantle, and the addition funnel was replaced with a condenser. The reaction mixture (a light orange solution or bright yellow solution) was then heated at 115-118° C. for 1.75-2 h. Additional gas evolution occurred at ca. 115° C. during this time. The reaction mixture was then cooled to room temperature with the aid of an ice-water bath and was then cooled further to 0° C. by adding ice directly into the reaction mixture. The solid that formed was collected on a Buchner funnel and was washed with cold water followed by a minimal amount of cold ethanol followed by a minimal amount of cold ether. The solid was then dried under vacuum to afford 3-methyl-5-nitropyridin-2-ol (53.5 g, 75% yield) as a pale yellow solid: mp 228-229° C.; $^1$H NMR (400 MHz, DMSO-d$_6$) δ 12.55 (s, br, 1H), 8.54 (d, J=3.0 Hz, 1H), 8.04 (d, J=2.0 Hz, 1H), 2.04 (s, 3H); $^{13}$C NMR (100 MHz, $CDCl_3$) δ 162.2, 135.4, 130.0, 129.5, 128.1, 15.8; LRMS, (ESI) nee 152.96 [(M−H)$^−$, calcd for $C_6H_5N_2O_3$, 153.03]. Anal. calcd. for $C_6H_6N_2O_3$: C, 46.75; H, 3.92; N, 18.17. Found: C, 46.80; H, 3.79; N, 18.14.

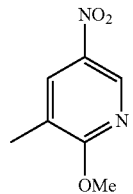

2-Methoxy-3-methyl-5-nitropyridine. 3-Methyl-5-nitropyridin-2-ol (134 g, 0.872 mol) (J. Org. Chem. 1949, 14, 328-332) was divided into 3 portions and placed in three 1-L round bottom flasks. $POCl_3$ (200 mL) was added to each flask and the mixtures were heated to reflux for 2 h. The solutions were cooled and the excess $POCl_3$ was removed in vacuo. The residues were poured into ice water (1 L) with stirring and the precipitates were collected by filtration and air dried for 20 min. The combined products were recrystallized from 10% ethyl acetate in hexanes (300 mL) and air dried to give 2-chloro-3-methyl-5-nitropyridine (139 g, 92% yield) as a white solid which was used in the next step without further purification: $^1$H NMR (300 MHz, $CDCl_3$) δ 9.04 (d, J=2.5 Hz, 1H), 8.33 (d, J=2.2 Hz, 1H), 2.50 (s, 3H).

2-Chloro-3-methyl-5-nitropyridine (139 g, 0.806 mol) from the above procedure was divided into two portions and placed in two 2-L round bottom flasks with methanol (500 mL). The solutions were cooled in dry ice/isopropanol baths as solid sodium methoxide (26.5 g, 0.467 mol) was added portion-wise to each flask so that the temperature was remained below 20° C. When the additions were complete, the resulting mixtures were heated to reflux for 1 h. The mixtures were cooled and diluted with ice water (500 mL) to give white precipitates, which were collected by filtration. The combined filtrates were washed with water and air dried to give 2-methoxy-3-methyl-5-nitropyridine (127 g, 97% yield) as a white solid: $^1$H NMR (400 MHz, CDCl$_3$) δ 8.91 (d, J=2.0 Hz, 1H), 8.16 (s, 1H), 4.06 (s, 3H), 2.25 (s, 3H); $^{13}$C NMR (100 MHz, CDCl$_3$) δ 165.83, 141.91, 139.37, 132.92, 121.77, 54.83, 15.84. An analytical sample was recrystallized from hexane to give white needles, mp 95-96.5° C. Anal. calcd. for C$_7$H$_8$N$_2$O$_3$: C, 50.00; H, 4.79; N, 16.66. Found: C, 49.73; H, 5.02; N, 16.48.

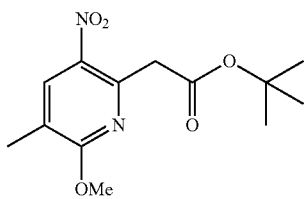 [SMILES: COc1nc(CC(=O)OC(C)(C)C)c([N+](=O)[O-])cc1C]

tert-Butyl 2-(6-methoxy-5-methyl-3-nitropyridin-2-yl)acetate. A yellow solution of 2-methoxy-3-methyl-5-nitropyridine (68.8 g, 409 mmol) and tert-butyl 2-chloroacetate (77.0 g, 511 mmol) in THF (1 L) was stirred and cooled to −20° C. in a dry ice/isopropanol bath. Potassium tert-butoxide (115 g, 1.02 mol) was added at a rate so that the reaction temperature was less than −10° C. The reaction mixture turned dark purple. When the addition was complete, the cooling bath was removed and the reaction was stirred for 30 min. The stirred reaction mixture was quenched with HCl (500 mL, 2.4 N). The purple solution turned pale yellow and the mixture separated into two layers. The organic layer was separated, washed three times with brine, and concentrated in vacuo. Hexane was added to the amber residue. The mixture was concentrated in vacuo and then dried under high vacuum for 1 hr to give tert-butyl 2-(6-methoxy-5-methyl-3-nitropyridin-2-yl)acetate (83.4 g, 72% yield) as a tan solid: $^1$H NMR (400 MHz, CDCl$_3$) δ 8.16 (s, 1H), 4.09 (s, 2H), 4.02 (s, 2H), 2.21 (s, 3H), 1.44 (s, 9H); $^{13}$C NMR (100 MHz, CDCl$_3$) δ 168.81, 163.63, 147.88, 139.41, 135.19, 120.82, 81.66, 54.69, 44.48, 28.03, 15.27. An analytical sample was recrystallized from hexane to give white needles, mp 71-72.5° C. Anal. calcd. for C$_{13}$H$_{18}$N$_2$O$_5$: C, 55.31; H, 6.42; N, 9.92. Found: C, 55.52; H, 6.40; N, 9.84.

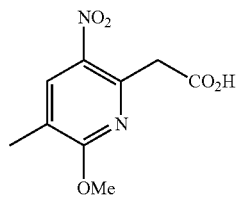 [SMILES: COc1nc(CC(=O)O)c([N+](=O)[O-])cc1C]

2-(6-Methoxy-5-methyl-3-nitropyridin-2-yl)acetic acid. A solution of tert-butyl 2-(6-methoxy-5-methyl-3-nitropyridin-2-yl)acetate (83.0 g, 294 mmol) in TFA (200 mL) was heated in a hot water bath for 1 h. The solution was concentrated in vacuo to give a brown oil. The oil was diluted with hexane and stirred. The resulting solid was collected by filtration and air dried to give 2-(6-methoxy-5-methyl-3-nitropyridin-2-yl) acetic acid (62.8 g, 94% yield) as a tan solid: $^1$H NMR (400 MHz, CDCl$_3$) δ 8.70 (s br, 1H), 8.20 (s, 1H), 4.25 (s, 2H), 4.03 (s, 3H), 2.24 (s, 3H); $^{13}$C NMR (100 MHz, CDCl$_3$) δ 175.59, 163.80, 146.52, 139.16, 135.30, 121.53, 54.86, 42.88, 15.32. An analytical sample was recrystallized from hexane: mp 135-137° C. Anal. calcd. for C$_9$H$_{10}$N$_2$O$_5$: C, 47.79; H, 4.46; N, 12.39. Found: C, 47.65; H, 4.14; N, 12.30.

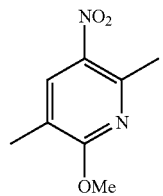

2-Methoxy-3,6-dimethyl-5-nitropyridine. A mixture of tert-butyl 2-(6-methoxy-5-methyl-3-nitropyridin-2-yl)acetate (62.5 g, 276 mmol), K$_2$CO$_3$ (20.0 g, 145 mmol), and DMF (100 mL) was heated with stirring in a hot water bath to 90° C. for 1 h. Gas evolution was noted during the heating period and had ceased after 1 hour. The mixture was poured into stirred ice water (600 mL), with washing of the reaction flask with a small volume of acetone. The resulting precipitate was collected by filtration and air dried to give 2-methoxy-3,6-dimethyl-5-nitropyridine (48.5 g, 96% yield) as a tan solid: $^1$H NMR (400 MHz, CDCl$_3$) δ 8.08 (s, 1H), 4.02 (s, 3H), 2.76 (d, 3H), 2.19 (s, 3H); $^{13}$C NMR (100 MHz, CDCl$_3$) δ 163.37, 151.63, 139.44, 135.02, 119.39, 54.45, 24.18, 15.16. An analytical sample was recrystallized from hexanes to give tan needles: mp 85.9-90.5° C. Anal. calcd. for C$_8$H$_{10}$N$_2$O$_3$: C, 52.74; H, 5.53; N, 15.37. Found: C, 52.82; Fr, 5.28; N, 15.45.

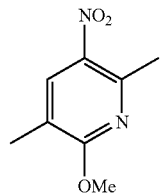

2-Methoxy-3,6-dimethyl-5-nitropyridine. Dimethyl sulfoxide (35 mL) was added to a dry round-bottomed flask containing NaH (1.82 g, 45.5 mmol, 60% in mineral oil). The resulting suspension was heated at 70° C. for 35 min during which time the suspension became a solution. The reaction mixture was cooled to room temperature, trimethylsulfoxonium iodide (10.0 g, 45.5 mmol) was added, and the mixture was stirred at room temperature for 30 min. 2-Methoxy-3-methyl-5-nitropyridine (4.50 g, 26.80 mmol) was added and the resulting dark red solution was stirred at room temperature for 30 min, at which time TLC showed complete consumption of starting material. The reaction mixture was transferred to a separatory funnel containing water (30 mL), and the aqueous layer was extracted with EtOAc (3×100 mL). The combined organic layers were washed with brine, dried over MgSO$_4$, filtered and concentrated. The residue was purified by MPLC (silica gel, 20% ethyl acetate in hexanes) to afford 2-methoxy-3,6-dimethyl-5-nitropyridine (2.00 g, 41% yield) as a colorless solid identical to that prepared by the previous method: mp 85.5-86.2° C.; $^1$H NMR (400 MHz, CDCl$_3$) δ 8.08 (s, 1H), 4.02 (s, 3H), 2.77 (s, 3H), 2.20 (s, 3H).

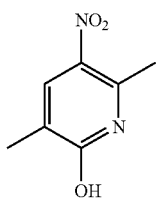

3,6-Dimethyl-5-nitropyridin-2-ol. A solution of 2-methoxy-3,6-dimethyl-5-nitropyridine (32.3 g, 182 mmol) in 12 N hydrochloric acid (300 mL) was heated at 100° C. for 1 h. Analysis by TLC indicated that some starting material remained, so the reaction was heated at 110° C. for an additional 45 min. The reaction mixture was cooled to room temperature and poured onto ice (400 g). When the ice had melted and the temperature of the resulting thick brown suspension was still less than 0° C., the mixture was filtered. The solid cake was washed with water (100 mL) and allowed to dry on the filter for 30 min. The solid was then resuspended in cold (−10° C.) ethanol (150 mL), filtered, washed with cold ethanol (50 mL), and air-dried on the filter for 1 h to afford 3,6-dimethyl-5-nitropyridin-2-ol (28.0 g, 94% yield) as a tan powder: mp 263° C.; $^1$H NMR (400 MHz, DMSO-$d_6$) δ 12.42 (s br, 1H), 8.03 (s, 1H), 2.61 (s, 3H), 2.01 (s, 3H); LRMS (ESI) m/e 169.3 [(M+H)$^+$, calcd for $C_7H_9N_2O_3$ 169.1]. Anal. calcd. for $C_7H_8N_2O_3$: C, 50.00; H, 4.79; N, 16.66. Found: C, 50.01; H, 4.59; N, 16.75.

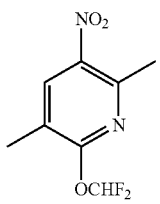

2-(Difluoromethoxy)-3,6-dimethyl-5-nitropyridine. Sodium hydride (6.63 g, 166 mmol, 60% in mineral oil) was washed with hexanes (100 mL) to remove the mineral oil and was then suspended in dry acetonitrile (1500 mL) at room temperature. 3,6-Dimethyl-5-nitropyridin-2-ol (27.9 g, 166 mmol) was added in portions over 30 minutes to give a yellow suspension. During the addition there was some bubbling but negligible temperature change. Cesium fluoride (2.50 g, 16.6 mmol) was then added followed by the slow addition of trimethylsilyl 2-(fluorosulfonyl)difluoroacetate (36.0 mL, 182 mmol) over 30 minutes. During the addition there was some bubbling, the temperature rose from 23° C. to 30° C., and the suspension became noticeably less turbid. After stirring for 15 min, TLC indicated that starting material still remained, so additional trimethylsilyl 2-(fluorosulfonyl)difluoroacetate (6.5 mL, 33 mmol) was added over 10 minutes. After an additional 15 min, TLC indicated consumption of starting material. The reaction was quenched by the addition of water (20 mL) dropwise at such a rate that the bubbling did not become too vigorous. After bubbling ceased, additional water (200 mL) was added. Most of the solvent was removed in vacuo and the aqueous residue was extracted with ethyl acetate (3×200 mL). The combined organic layers were dried over $Na_2SO_4$ and evaporated to a brown syrup which solidified upon standing. This residue was dissolved in ethanol (400 mL) and decolorizing charcoal (15 g) was added. The suspension was heated at 70° C. for 20 min and then filtered through a pad of Celite and sand. The filtrate was collected and the solvent was evaporated. The residue was dissolved in methylene chloride and the solution was evaporated to give 2-(difluoromethoxy)-3,6-dimethyl-5-nitropyridine (33.4 g, 92% yield) as a pale yellow solid: mp 51-52° C.; $^1$H NMR (400 MHz, CDCl$_3$) δ8.21 (s, 1H), 7.55 (t, J=72.0 Hz, 1H), 2.76 (s, 3H), 2.30 (s, 3H). Anal. calcd. for $C_8H_8N_2O_3F_2$: C, 44.04; H, 3.69; N, 12.84. Found: C, 43.78; H, 3.55; N, 12.58.

Alternate route. To a suspension of 3,6-methyl-5-nitropyridin-2-ol (700 mg, 4.17 mmol) in acetonitrile (70 mL) was added NaH (450 mg, 11.3 mmol, 60% in mineral oil). After stirring at room temperature for 15 min, 2,2-difluoro-2-(fluorosulfonyl)acetic acid (0.73 mL, 7.09 mmol) was added dropwise over several minutes. Some bubbling occurred during the addition. After stirring the reaction mixture at room temperature for 15 min, the reaction was quenched by the slow addition of water (10 mL). The acetonitrile was removed in vacuo and the residue was transferred to a separatory funnel containing water (50 mL). The aqueous layer was extracted with EtOAc (3×50 mL). The combined organic layers were washed with brine, dried over MgSO$_4$, filtered and concentrated. The residue was purified by MPLC on silica gel (10% ethyl acetate in hexanes) to afford 2-(difluoromethoxy)-3,6-dimethyl-5-nitropyridine (870 mg, 96% yield) as a colorless solid identical to that prepared by Method A: mp 48-49° C.; $^1$H NMR (400 MHz, CDCl$_3$) δ 8.21 (s, 1H), 7.54 (t, J=72.4 Hz, 1H), 2.76 (s, 3H), 2.30 (s, 3H); $^{13}$C NMR (100 MHz, CDCl$_3$) δ 158.1, 151.0, 142.0, 137.0, 120.0, 113.9 (t, J=255.8 Hz), 23.5, 14.7.

6-(Difluoromethoxy)-2,5-dimethylpyridin-3-amine. To a solution of 2-(difluoromethoxy)-3,6-dimethyl-5-nitropyridine (33.4 g, 153 mmol) in methylene chloride (100 mL) and ethanol (600 mL) was added 10% palladium on charcoal (3.3 g). The resulting suspension was hydrogenated on a Parr device at 40 psi H$_2$ for 1 h. TLC was used to monitor the reaction. Additional 3.3 g of palladium on charcoal were added hourly until no starting material remained. A total of 13.2 g of Pd/C was added. The reaction mixture was kept under an H$_2$ atmosphere for 2 h after the last addition of catalyst. The reaction mixture was filtered through Celite and sand and the collected solids were washed with ethyl acetate (2×100 mL). The filtrate was concentrated in vacuo to give a grey oil, which was purified by column chromatography on silica gel (35%→50% ethyl acetate in hexanes) to furnish 6-(difluoromethoxy)-2,5-dimethylpyridin-3-amine (25.7 g, 89% yield) as a pale yellow oil which solidified upon cooling in a refrigerator. The product was recrystallized from hexanes below 0° C. to afford white needles: mp 40-42° C.; $^1$H NMR (400 MHz, CDCl$_3$) δ 7.35 (1, J=74.0 Hz, 1H), 6.84 (s, 1H), 2.27 (s, 3H), 2.15 (s, 3H); LRMS (ESI) m/e 189.2 [(M+H)$^+$, calcd for $C_8H_{11}N_2OF_2$ 189.1]. Anal calcd. for $C_8H_{10}N_2OF_2$: C, 51.12; H, 5.38; N, 14.86. Found: C, 51.17; H, 5.29; N, 14.87.

Alternate route. To a solution of 2-(difluoromethoxy)-3,6-dimethyl-5-nitropyridine (1.00 g, 4.58 mmol) in EtOH (40 mL) and acetic acid (4 mL) was added iron powder (1.26 g, 22.9 mmol). The reaction mixture was heated at a vigorous reflux with the aid of a heating mantle in a flask without a stir bar. After 1.75 h, the reaction mixture was cooled to room temperature and the iron powder was removed by filtration through a pad of Celite. The filtrate was concentrated and the residue was transferred to a separatory funnel containing saturated aqueous NaHCO$_3$ (50 mL). The aqueous layer was extracted with EtOAc (3×100 mL). The combined organic layers were washed with brine, dried over MgSO$_4$, filtered and concentrated. The residue was purified by MPLC on silica gel (20%→50% ethyl acetate in hexanes) to afford 6-(difluoromethoxy)-2,5-dimethylpyridin-3-amine (774 mg, 90% yield) as a pale yellow solid identical to that prepared by Method A: mp 38.4-39.4° C.; $^1$H NMR (400 MHz, CDCl$_3$) δ 7.35 (t, J=74.5 Hz, 1H), 6.82 (s, 1H), 2.26 (s, 3H), 2.14 (s, 3H); $^{13}$C NMR (100 MHz, CDCl$_3$) δ 149.6, 137.4, 137.1, 127.4, 119.0, 115.0 (J=251.3 Hz), 19.3, 14.8; LRMS (ESI) m/e 189.0 [(M+H)$^+$, calcd for C$_8$H$_{11}$N$_2$OF$_2$ 189.1].

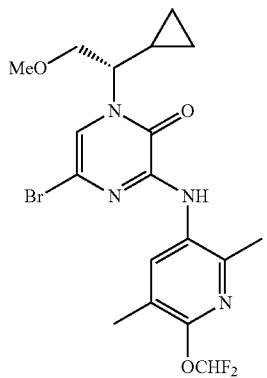 [SMILES: COC[C@H](C1CC1)n1cc(Br)nc(Nc2cc(C)c(OC(F)F)nc2C)c1=O]

(S)-5-Bromo-1-(cyclopropyl-2-methoxyethyl)-3-[6-(difluoromethoxy)-2,5-dimethyl-pyridin-3-ylamino]pyrazin-2(1H)-one. (S)-3,5-Dibromo-1-(1-cyclopropyl-2-methoxyethyl)pyrazin-2(1H)-one (18.1 g, 51.7 mmol) and 6-(difluoromethoxy)-2,5-dimethylpyridin-3-amine (9.70 mg, 51.7 mmol) were combined in a 2 L, 3-necked round bottom flask equipped with a thermometer and an addition funnel and placed under N$_2$. THF (360 mL) was added and the mixture was cooled to 0° C. NaHMDS (109 mL, 109 mmol, 1 M in THF) was added dropwise via the addition funnel over 15 min (the internal temperature was maintained below 5° C.). After the addition was complete, the reaction mixture was stirred at 0° C. for an additional 30 min. The reaction was quenched by the addition of saturated aqueous NH$_4$Cl (120 mL). The mixture was transferred to a separatory funnel containing water (100 mL) and the aqueous layer was extracted with ethyl acetate (3×250 mL). The combined organic layers were washed with brine, dried over MgSO$_4$, filtered and concentrated to afford (S)-5-bromo-1-(cyclopropyl-2-methoxyethyl)-3-[6-(difluoromethoxy)-2,5-dimethylpyridin-3-ylamino]pyrazin-2(1H)-one (22.4 g, 95% yield) as a brown solid which was used in the next step without further purification: $^1$H NMR (400 MHz, CDCl$_3$) δ 8.40 (s, 1H), 7.98 (s, 1H), 7.53 (s, 1H), 7.46 (t, J=73.7 Hz, 1H), 4.16-4.12 (m, 1H), 3.74 (dd, J$_{AB}$=10.5, J$_{AX}$=5.2 Hz, 1H), 3.66 (dd, J$_{BA}$=10.3, J$_{BX}$=3.3 Hz, 1H), 3.35 (s, 3H), 2.44 (s, 3H), 2.27 (s, 3H), 1.39-1.34 (m, 1H), 0.85-0.79 (m, 1H), 0.66-0.62 (m, 1H), 0.56-0.51 (m, 1H), 0.34-0.29 (m, 1H); HRMS (ESI) m/e 459.0864 [(M+H)$^+$, calcd for C$_{18}$H$_{22}$N$_4$O$_3$BrF$_2$ 459.0843].

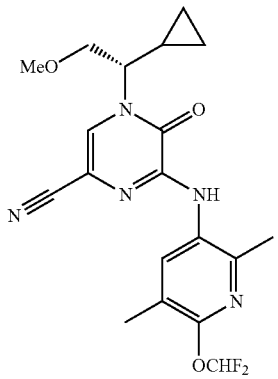 [SMILES: COC[C@H](C1CC1)n1cc(C#N)nc(Nc2cc(C)c(OC(F)F)nc2C)c1=O]

(S)-4-(1-Cyclopropyl-2-methoxyethyl)-6-[6-(difluoromethoxy)-2,5-dimethylpyridin-3-ylamino]-5-oxo-4,5-dihydropyrazine-2-carbonitrile. (S)-5-Bromo-1-(cyclopropyl-2-methoxyethyl)-3-[6-(difluoromethoxy)-2,5-dimethylpyridin-3-ylamino]pyrazin-2(1H)-one (22.4 g, 48.8 mmol) was dissolved in anhydrous dimethylformamide (480 mL) and water (24 mL) at room temperature with magnetic stirring. Nitrogen was bubbled through the reaction mixture for 15 minutes. Zinc cyanide (6.00 g, 51.0 mmol), Pd$_2$(dba)$_3$ (2.23 g, 2.40 mmol) and dppf (3.24 g, 5.85 mmol) were added and the reaction mixture was heated at 120° C. for 3 h. The reaction was cooled and filtered through a pad of Celite. The DMF filtrate was evaporated in vacuo (bath temperature <40° C.) and the residue was transferred to a separatory funnel containing saturated aqueous NH$_4$Cl solution (200 mL). The aqueous layer was extracted with EtOAc (3×400 mL). The combined organic layers were washed with brine (300 mL), dried over MgSO$_4$, filtered and concentrated. Purification by column chromatography on silica gel (70%→100% CH$_2$Cl$_2$ in hexanes then 2%→5% ethyl acetate in CH$_2$Cl$_2$) afforded (S)-4-(1-cyclopropyl-2-methoxyethyl)-6-[6-(difluoromethoxy)-2,5-dimethylpyridin-3-ylamino]-5-oxo-4,5-dihydropyrazine-2-carbonitrile (14.2 g, 72% yield) as a pale yellow solid. Recrystallization from a mixture of EtOH:2-BuOH (10:1) afforded pale yellow needles: mp 146.8-147.7° C.; [α]$^{25}_D$ −63.7 (c 0.486, CHCl$_3$); $^1$H NMR (400 MHz, CDCl$_3$) δ 8.40 (s, 1H), 7.98 (s, 1H), 7.53 (s, 1H), 7.46 (t, J=73.5 Hz, 1H), 4.16-4.12 (m, 1H), 3.74 (dd, J$_{AB}$=10.3, J$_{AX}$=5.0 Hz, 1H), 3.67 (dd, J$_{BA}$=10.4, J$_{BX}$=3.0 Hz, 1H), 3.35 (s, 3H), 2.44 (s, 3H), 2.27 (s, 3H), 1.39-1.33 (m, 1H), 0.85-0.79 (m, 1H), 0.67-0.61 (m, 1H), 0.56-0.50 (m, 1H), 0.34-0.29 (m, 1H); HRMS (ESI) m/e 406.1704 [(M+H)$^+$, calcd for C$_{19}$H$_{22}$N$_5$O$_3$F$_2$ 406.1691]. Anal. Calcd for C$_{19}$H$_{21}$N$_5$O$_3$F$_2$: C, 56.29; H, 5.22; N, 17.27. Found: C, 56.38; H, 5.31; N, 17.34.

(S)-4-(1-cyclopropyl-2-methoxyethyl)-6-[6-(difluoromethoxy)-2,5-dimethylpyridin-3-ylamino]-5-oxo-4,5-dihydropyrazine-2-carbonitrile (97 g, from multiple runs) enhanced in the first eluting isomer (~97% enantiomeric purity) was combined for removal of the undesired second eluting isomer by super critical fluid chromatography (SFC) on chiral support: Chiralpak OD-H column (5×25 cm), mobile phase=15% isopropanol/acetonitrile (1:1) in CO$_2$; flow rate=200 mL/min, pressure=100 bar, temperature=35° C., λ=254 nm, 5 mL of 91 mg/mL in isopropanol/acetonitrile (1:1) per injection per 6 min. The purified material had an optical purity >99% ee as determined by analytical SFC: Chiralcel OD-H column (4.6×250 mm, 5 μm); mobile phase=8% ethanol in CO$_2$; flow rate=2 mL/min @ 150 bars; λ=215 nm; t$_R$=6.5 min.

The separation provided 85 g of enantiomerically pure compound (ee >99%). This material was divided into 3 portions of ~28 grams each. Each portion was recrystallized from anhydrous 2-butanol (280 mL). The combined solids were dried under high vacuum for 72 hours to provide 81.7 grams of (S)-4-(1-cyclopropyl-2-methoxyethyl)-6-[6-(difluoromethoxy)-2,5-dimethylpyridin-3-ylamino]-5-oxo-4,5-dihydropyrazine-2-carbonitrile.

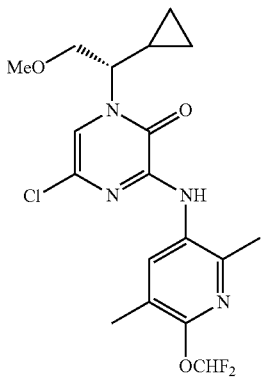 [SMILES: COC[C@H](C1CC1)n1cc(Cl)nc(Nc2cc(C)c(OC(F)F)nc2C)c1=O]

(S)-5-Chloro-1-(cyclopropyl-2-methoxyethyl)-3-[6-(difluoromethyl)-2,5-dimethyl-pyridin-3-ylamino]pyrazin-2 (1H)-one (S)-3,5-Dichloro-1-(1-cyclopropyl-2-methoxyethyl)pyrazin-2(1H)-one (15.0 g, 57.0 mmol) and 6-(difluoromethoxy)-2,5-dimethylpyridin-3-amine (10.7 g, 57.0 mmol) were combined under N$_2$ in a 2 L, 3-neck, round-bottomed flask equipped with a thermometer and an addition funnel. THF (570 mL) was added and the mixture was cooled to 0° C. NaHMDS (119.7 mL, 119.7 mmol, 1 M in THF) was added dropwise via addition funnel over 20 min at a rate to maintain the internal temperature below 5° C. After the addition was complete, the reaction mixture was stirred at 0° C. for an additional 15 min. The reaction was quenched by the addition of saturated aqueous NH$_4$Cl (60 mL). The mixture was transferred to a separatory funnel containing water (400 mL) and the aqueous layer was extracted with ether (3×300 mL). The combined organic layers were washed with brine, dried over MgSO$_4$, filtered and concentrated. The product was purified by column chromatography on silica gel (30% ethyl acetate in hexanes) to afford (S)-5-chloro-1-(cyclopropyl-2-methoxyethyl)-3-[6-(difluoromethoxy)-2,5-dimethylpyridin-3-ylamino]pyrazin-2(1H)-one (22.1 g, 94% yield) as a pale yellow solid which was subsequently recrystallized from heptane to furnish colorless needles: mp 103.4-104.4° C.; [α]$^{25}_D$ −41.9 (c 0.807, CHCl$_3$); $^1$H NMR (400 MHz, CDCl$_3$) δ 8.42 (s, 1H), 8.02 (s, 1H), 7.46 (t, J=74.0 Hz, 1H), 6.96 (s, 1H), 4.19-4.14 (m, 1H), 3.75 (dd, J$_{AB}$=10.3, J$_{AX}$=6.3 Hz, 1H), 3.67 (dd, J$_{BA}$=10.3, J$_{BX}$=3.5 Hz, 1H), 3.34 (s, 3H), 2.44 (s, 3H), 2.26 (s, 3H), 1.32-1.26 (m, 1H), 0.81-0.74 (m, 1H), 0.63-0.54 (m, 1H), 0.52-0.47 (m, 1H), 0.36-0.29 (m, 1H); HRMS (ESI) m/e 415.1360 [(M+H)$^+$, calcd for C$_{18}$H$_{22}$N$_4$O$_3$ClF$_2$ 415.1349]. Anal. Calcd for C$_{18}$H$_{21}$N$_4$O$_3$ClF$_2$: C, 52.11; H, 5.10; N, 13.50. Found: C, 52.05; H, 4.99; N, 13.48.

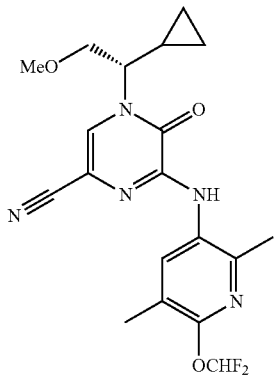 [SMILES: COC[C@H](C1CC1)n1cc(C#N)nc(Nc2cc(C)c(OC(F)F)nc2C)c1=O]

(S)-4-(1-Cyclopropyl-2-methoxyethyl)-6-[6-(difluoromethoxy)-2,5-dimethylpyridin-3-ylamino]-5-oxo-4,5-dihydropyrazine-2-carbonitrile. (S)-5-Chloro-1-(cyclopropyl-2-methoxyethyl)-3-[6-(difluoromethoxy)-2,5-dimethylpyridin-3-ylamino]pyrazin-2(1H)-one (99.3 mg, 0.24 mmol) was dissolved in anhydrous NMP (3 mL). To this solution was added Pd(dppf)Cl$_2$.CH$_2$Cl$_2$ (78.4 mg, 0.096 mmol), Zn(CN)$_2$ (60 mg, 0.51 mmol) and Zn powder (24 mg, 0.37 mmol). N$_2$ was bubbled through the reaction mixture for 15 min to expel the dissolved O$_2$ and the reaction mixture was maintained at 120° C. under Argon for 1 h. LC-MS analysis indicated a 92.5% conversion to required product. LRMS (ESI) m/e 406.3 [(M+H)$^+$, calcd for C$_{19}$H$_{22}$N$_5$O$_3$F$_2$ 406.2].

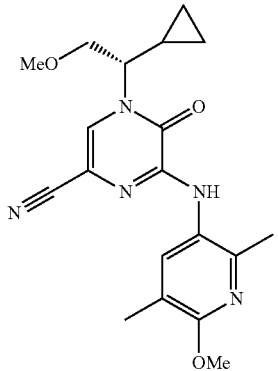 [SMILES: COC[C@H](C1CC1)n1cc(C#N)nc(Nc2cc(C)c(OC)nc2C)c1=O]

(S)-4-(1-Cyclopropyl-2-methoxyethyl)-6-(6-methoxy-2,5-dimethylpyridin-3-ylamino)-5-oxo-4,5-dihydropyrazine-2-carbonitrile. (S)-5-Chloro-1-(cyclopropyl-2-methoxyethyl)-3-[6-(methoxy)-2,5-dimethyl-pyridin-3-ylamino] pyrazin-2(1H)-one (3.00 g, 7.93 mmol) was dissolved in 63 mL of N-methylpyrrolidinone. Pd(dppf)Cl$_2$.CH$_2$Cl$_2$ (648 mg, 0.793 mmol), Zn(CN)$_2$ (1.86 g, 15.9 mmol) and Zn powder (619 mg, 9.52 mmol) were added to the solution. After bubbling N$_2$ through the solution for 15 min, the dark mixture was maintained under argon at 120° C. for 23 h. LC-MS analysis of the reaction mixture revealed a 98.6% conversion. The reaction mixture was cooled to ambient temperature, filtered through a short bed of Celite and the Celite cake was washed with NMP. The filtrate was evaporated in vacuo (bath temperature ~60° C.). The dark residue was partitioned between EtOAc (350 mL) and H$_2$O (60 mL). The organic layer was washed with water (2×50 mL) and brine (50 mL), dried over Na$_2$SO$_4$, and then evaporated in vacuo. The dark brown residue was then purified by column chromatography on silica gel (30% ethyl acetate in hexanes, R$_f$=0.3) to give pure (S)-4-(1-cyclopropyl-2-methoxyethyl)-6-(6-methoxy-2,5-dimethylpyridin-3-ylamino)-5-oxo-4,5-dihydropyrazine-2-carbonitrile (2.83 g, 96.5%) as pale yellow solid: $^1$H NMR (CDCl$_3$) δ 7.86 (s, 1H), 7.49 (s, 1H), 4.16-4.13 (m, 1H), 3.94 (s, 1H), 3.74 (dd, 1H, J$_{AB}$=10.4 Hz, J$_{AX}$=5.2 Hz), 3.66 (dd, J$_{BX}$=3.2 Hz), 3.35 (s, 3H), 2.43 (s, 3H), 2.19 (s, 3H), 1.39-1.32 (m, 1H), 0.85-0.79 (m, 1H), 0.67-0.61 (m, 1H), 0.55-0.50 (m, 1H), 0.34-0.29 (m, 1H); $^{13}$C NMR (CDCl$_3$): 158.7, 151.4, 148.1, 144.1, 133.1, 125.7, 124.7, 118.4, 117.3, 107.8, 77.4, 77.1, 76.9, 72.7, 62.3, 59.5, 53.6, 20.0, 15.8, 11.2, 6.2, 4.1; LRMS (ESI) m/e 370 [(M+H)$^+$, calcd for C$_{19}$H$_{24}$N$_5$O$_3$ 370]; t$_R$=2.0 min (Solvent A: MeOH:H$_2$O:TFA=10:90:0.1; Solvent B: MeOH:H$_2$O:TFA=90:10:0.1; 40% B in A to 100% B in A linear gradient in a 3 min run with 1 min hold time at the end, λ=280 nm).

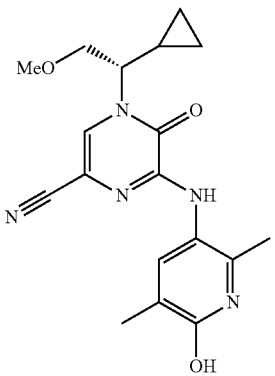 [SMILES: COC[C@H](C1CC1)n1cc(C#N)nc(Nc2cc(C)c(O)nc2C)c1=O]

(S)-4-(1-Cyclopropyl-2-methoxyethyl)-6-(6-hydroxy-2,5-dimethylpyridin-3-ylamino)-5-oxo-4,5-dihydropyrazine-2-carbonitrile. (S)-4-(1-Cyclopropyl-2-methoxyethyl)-6-(6-methoxy-2,5-dimethylpyridin-3-ylamino)-5-oxo-4,5-dihydropyrazine-2-carbonitrile (3.00 g, 8.12 mmol) and KI (6.2 g, 37.3 mmol) in glacial acetic acid (80 mL) was heated at 100° C. with stirring for 1 h. LC-MS analysis indicated >98% conversion to the required product. The reaction mixture was cooled to ambient temperature and acetic acid was evaporated in vacuo. The residue was partitioned between ethyl acetate (3×150 mL) and H$_2$O (~100 mL). The organic layer was washed with brine (100 mL) and then dried over Na$_2$SO$_4$. The organic layer was evaporated in vacuo and the dark brown residue was purified by Biotage SiO$_2$ column chromatography (5% MeOH/CH$_2$Cl$_2$, R$_f$=0.16) to give pure (S)-4-(1-cyclopropyl-2-methoxyethyl)-6-(6-hydroxy-2,5-dimethylpyridin-3-ylamino)-5-oxo-4,5-dihydropyrazine-2-carbonitrile (2.33 g, 81%) as pale yellow solid: $^1$H NMR (CDCl$_3$) δ 7.85-7.55 (br. s, 1H), 7.48 (s, 1H), 4.16-4.12 (m, 1H), 3.73 (dd, 1H, J$_{AB}$=10.3 Hz, J$_{AX}$=4.9 Hz), 3.66 (dd, J$_{BX}$=2.2 Hz), 3.35 (s, 3H), 2.40-2.20 (br s, 6H), 1.39-1.32 (m, 1H), 0.85-0.79 (m, 1H), 0.67-0.61 (m, 1H), 0.55-0.51 (m, 1H), 0.34-0.29 (m, 1H); LRMS (ESI) m/e 356 [(M+H)$^+$, calcd for C$_{18}$H$_{21}$N$_5$O$_3$ 356]; t$_R$=1.8 min (Solvent A: MeOH:H$_2$O:TFA=10:90:0.1; Solvent B: MeOH:H$_2$O:TFA=90:10:0.1; 0% B in A to 100% B in A linear gradient in a 3 min run with 1 min hold time at the end, λ=280 nm).

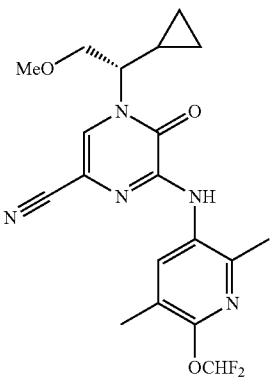 [SMILES: COC[C@H](C1CC1)n1cc(C#N)nc(Nc2cc(C)c(OC(F)F)nc2C)c1=O]

(S)-4-(1-Cyclopropyl-2-methoxyethyl)-6-(6-(difluoromethoxy)-2,5-dimethylpyridin-3-ylamino)-5-oxo-4,5-dihydropyrazine-2-carbonitrile. A mixture of pure (S)-4-(1-cyclopropyl-2-methoxyethyl)-6-(6-hydroxy-2,5-dimethylpyridin-3-ylamino)-5-oxo-4,5-dihydropyrazine-2-carbonitrile (2.3 g, 6.5 mmol) and CsF (395 mg, 2.6 mmol) was added to acetonitrile (65 mL). To the resulting suspension, trimethylsilyl 2,2-difluoro-2-(fluorosulfonyl)acetate (3.82 mL, 19.4 mmol) was slowly added (use extreme caution! The reagent can cause dermatological damage and should always be handled in hood). LC-MS analysis after 1 h showed the reaction to be complete (89% conversion to required product). Volatiles were evaporated in vacuo and the residue was partitioned between EtOAc (3×120 mL) and H$_2$O (~100 mL). The organic layer was washed with water (2×50 mL) and brine (50 mL), and dried over Na$_2$SO$_4$. The ethyl acetate was evaporated in vacuo and the residue was dissolved in DMF (10 mL). The solution was applied to C$_{18}$ silica gel column (14 cm×5 cm) equilibrated with MeCN:H$_2$O (1:2). The column was eluted with 33% MeCN/H$_2$O (500 mL), 45% MeCN/H$_2$O (500 mL), 60% MeCN/H$_2$O (1000 mL), 70% MeCN/H$_2$O (500 mL). Individual fractions were analyzed by LC-MS (product comes out in between 60%-70% MeCN/H$_2$O). Fractions containing pure product were combined and concentrated in vacuo to give pure (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile (2.28 g, 87% yield) as pale yellow solid: $^1$H NMR (CDCl$_3$) δ 8.43 (s, 1H); 8.01 (s, 1H); 7.56 (s, 1H); 7.49 (t, J$_{H-F}$=73.8 Hz, 1H); 4.15-4.18 (m, 1H); 3.76 (dd, J$_{AB}$=10.4, J$_{AX}$=5.2 Hz, 1H); 3.68 (dd, J$_{BA}$=10.4, J$_{BX}$=3.1 Hz, 1H); 3.37 (s, 3H); 2.46 (s, 3H); 2.30 (s, 3H); 1.35-1.42 (m, 1H); 0.82-0.88 (m, 1H); 0.64-0.69 (m, 1H); 0.53-0.58 (m, 1H); 0.31-0.36 (m, 1H); $^{13}$C NMR (126 MHz, CDCl$_3$) δ 153.0, 151.5, 147.8, 143.8, 133.3, 129.4, 125.6, 119.1, 117.2, 114.8 (t, J=256.1 Hz, 1 C), 107.6, 72.7, 62.6, 59.6, 20.0, 15.5, 11.4, 6.4, 4.2; $^{19}$F NMR (CDCl$_3$) δ −88.73 (d); LRMS (ESI) m/e 406 [(M+H)$^+$, calcd for C$_{19}$H$_{22}$N$_5$O$_3$F$_2$ 406]; t$_R$=2.7 min (Solvent A: MeOH:H$_2$O:TFA 10:90:0.1; Solvent MeOH:H$_2$O:TFA=90:10:0.1; 40% B in A to 100% B in A linear gradient in a 3 min run with 1 min hold time at the end, λ=280 nm).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A method for the treatment of depression, anxiety or an anxiety related disorder, irritable bowel syndrome, addiction or negative aspects of drug and alcohol withdrawal which comprises administering a therapeutically effective amount of (S)-4-(1-cyclopropyl-2-methoxyethyl)-6-(6-(difluoromethoxy)-2,5-dimethylpyridin-3-ylamino)-5-oxo-4,5-dihydropyrazine-2-carbonitrile, or a pharmaceutically acceptable salt thereof, to a patient.

2. The method of claim 1 where the condition is depression.

3. The method of claim 1 where the condition is anxiety or an anxiety related disorder.

4. The method of claim 1 where the condition is irritable bowel syndrome.

5. The method of claim 1 where the condition is addiction or negative aspects of drug and alcohol withdrawal.

* * * * *